(12) United States Patent
Brinker et al.

(10) Patent No.: US 10,774,341 B2
(45) Date of Patent: *Sep. 15, 2020

(54) COTTON TRANSGENIC EVENT MON 88701 AND METHODS OF USE THEREOF

(71) Applicant: MonsantoTechnology LLC, St. Louis, MO (US)

(72) Inventors: Ronald Joseph Brinker, Ellisville, MO (US); Wen C. Burns, Chesterfield, MO (US); Paul C. C. Feng, Creve Coeur, MO (US); John A. Kendig, Chesterfield, MO (US); Sherry LeClere, Ballwin, MO (US); Jennifer Lutke, Ballwin, MO (US); Marianne Malven, Ellisville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/013,480

(22) Filed: Jun. 20, 2018

(65) Prior Publication Data

US 2018/0363068 A1 Dec. 20, 2018

Related U.S. Application Data

(60) Continuation of application No. 14/676,691, filed on Apr. 1, 2015, now Pat. No. 10,030,277, which is a division of application No. 14/222,352, filed on Mar. 21, 2014, now Pat. No. 9,024,115, which is a division of application No. 13/419,127, filed on Mar. 13, 2012, now Pat. No. 8,735,661.

(60) Provisional application No. 61/469,118, filed on Mar. 30, 2011.

(51) Int. Cl.
*C12N 15/82* (2006.01)

(52) U.S. Cl.
CPC ..... *C12N 15/8274* (2013.01); *C12N 15/8277* (2013.01)

(58) Field of Classification Search
None
See application file for complete search history.

(56) References Cited

U.S. PATENT DOCUMENTS

| 7,166,771 B2 * | 1/2007 | Eenennaam | C12N 15/8216 536/23.1 |
|---|---|---|---|
| RE46,292 E | 1/2017 | Brinker et al. | |
| 2003/0097687 A1 * | 5/2003 | Trolinder | C07K 14/415 800/284 |
| 2006/0059590 A1 | 3/2006 | Cerny et al. | |
| 2010/0323893 A1 | 12/2010 | Ikeda | |
| 2019/0055575 A1 | 2/2019 | Burns et al. | |

FOREIGN PATENT DOCUMENTS

| CN | 1551920 A | 12/2004 |
|---|---|---|
| CN | 101466837 A | 6/2009 |
| CN | 101500421 A | 8/2009 |
| CN | 101528033 A | 9/2009 |
| EP | 2118290 | 5/2013 |
| WO | WO 1998/045424 | 10/1998 |
| WO | WO 03/013224 A2 | 2/2003 |
| WO | WO 2004/072235 A2 | 8/2004 |
| WO | WO 2007/047016 | 4/2007 |
| WO | WO 2007/143690 | 12/2007 |
| WO | WO 2008/051633 | 5/2008 |
| WO | WO 2009/085982 A1 | 7/2009 |
| WO | WO 2010/085705 | 7/2010 |
| WO | WO 2011/034704 | 3/2011 |

OTHER PUBLICATIONS

Behrens et al., "Dicamba resistance: Enlarging and preserving biotechnology-based weed management strategies," *Science*, 316:1185-1188, 2007.
Herman et al., "A three-component dicamba 0-demethylase from *Pseudomonas maltophilia*, Strain DI-6," *J Bio Chem*, 280(26):24759-24767, 2005.
Wang et al., "A three-component enzyme system catalyzes the O demethylase of the herbicide dicamba in *Pseudomonas maltophilia* DI-6," *Appl Environ Microbiol*, 63(4):1623-1626, 1997.
Krueger et al., Isolation and identification of microorganisms for the degradation of dicamba, *J Agric Food Chem*, 37:534-538, 1989.
Subramanian et al., "Engineering dicamba selectivity in crops: a search for appropriate degradative enzymes(s)," *J Industr Microbiol Biotech*, 19:344-349, 1997.
Bartsch et al., "Initial steps in the degradation of phosphinothricin (glufosinate) by soil bacteria," *Appl Environ Microbiol*, 55(3):711-716, 1989.
DeBlock et al., "Engineering herbicide resistance in plants by expression of a detoxifying enzyme," *EMBO J*, 6(9):2513-2518, 1987.
Herouet et al., "Safety evaluation of the phosphinothricin acetyltransferase proteins encoded by the pat and bar sequences that confer tolerance to glufosinate-ammonium herbicide in transgenic plants," *Regulatory Toxicol and Pharmacol*, 41:134-149, 2005.

(Continued)

*Primary Examiner* — Mykola V. Kovalenko
(74) *Attorney, Agent, or Firm* — Dentons US LLP; Lawrence Lavin

(57) ABSTRACT

The invention provides cotton event MON 88701, and plants, plant cells, seeds, plant parts, and commodity products comprising event MON 88701. The invention also provides polynucleotides specific for event MON 88701 and plants, plant cells, seeds, plant parts, and commodity products comprising polynucleotides specific for event MON 88701. The invention also provides methods related to event MON 88701.

2 Claims, 7 Drawing Sheets

Specification includes a Sequence Listing.

(56) References Cited

OTHER PUBLICATIONS

Organization for Economic Co-operation and Development, "Consensus document on general information concerning the genes and their enzymes that confer tolerance to phosphinothricin herbicide," OECD Environmental Health and Safety Publications, Series on Harmonization of Regulatory Oversight of Biotechnology, No. 11, 1-26, Jun. 1, 1999.
Thompson et al., "Characterization of the herbicide-resistance gene bar from *Streptomyces hygroscopicus*," *EMBO J*, 6:2519-2523, 1987.
Wehrman et al., "The similarities of bar and pat gene products make them equally applicable for plant engineers," *Nature Biotech*, 14:1274-1278, 1996.
Doherty et al., "Palmer Amaranth control with dicamba and glufosinate as influenced by weed size and herbicide rate," *Summ of Arkansas Cotton Res*, 582:105-107, 2009.
Hohe et al. "A tool for understanding homologous recombination in plants," *Plant Cell Rep*. 21:1135-1142, 2003.
Wang et al., "Characterization of Cellular and Enzymatic Degradation of Dicamba by Pseudomonas maltophilia, Strain DI-6," dissertation presented to the Faculty of the Graduate Collage at the University of Nebraska, 1996.
CLARITY herbicide Specimen Label, BASF, "For weed control in asparagus, conservation reserve programs, corn, cotton, fallow croplands, general farmstead (noncropland), sorghum, grass grown for seed, hay, proso millet, pasture, rangeland, small grains, sod farms and farmstead turf, soybean, and sugarcane," 2010.
York et al., "Response of Strip-tilled Cotton to Preplant Applications of Dicamba and 2,4-D," *The Journal of Cotton Science* 8:213-222, 2004.
Roche, PCR Methods Manual, 3rd Edition, p. 199, 2006.

\* cited by examiner

A

B

A

B

COTTON TRANSGENIC EVENT MON 88701 AND METHODS OF USE THEREOF

CROSS REFERENCE TO RELATED APPLICATIONS

This application is a continuation of U.S. patent application Ser. No. 14/676,691, filed Apr. 1, 2015, which application is a divisional of U.S. patent application Ser. No. 14/222,352, filed Mar. 21, 2014, now issued as U.S. Pat. No. 9,024,115, which application is a divisional of U.S. patent application Ser. No. 13/419,127 filed Mar. 13, 2012, now issued as U.S. Pat. No. 8,735,661 which claims the benefit of U.S. Provisional Application No. 61/469,118, filed on Mar. 30, 2011, each of which is herein incorporated by reference in its entirety.

INCORPORATION OF SEQUENCE LISTING

The sequence listing contained in the file named "MONS302US.txt", which is 21 kilobytes (size as measured in Microsoft Windows®) and was created on Mar. 9, 2012, is filed herewith by electronic submission and is incorporated by reference herein.

FIELD OF THE INVENTION

The invention relates to transgenic *Gossypium hirsutum* event MON 88701. The event exhibits tolerance to dicamba and glufosinate herbicides. The invention also relates to plants, plant parts, plant seeds, plant cells, agricultural products, and methods related to event MON 88701 and provides nucleotide molecules that are unique to the event and were created in connection with the insertion of transgenic DNA into the genome of a *Gossypium hirsutum* plant.

BACKGROUND OF THE INVENTION

Cotton (*Gossypium hirsutum*) is an important crop in many areas of the world, and the methods of biotechnology have been applied to this crop in order to produce cotton with desirable traits. One such desirable trait is herbicide tolerance. The expression of an herbicide tolerance transgene in a plant can confer the desirable trait of herbicide tolerance on the plant, but expression of the transgene may be influenced by the chromosomal location and the genomic result of the transgene insertion. For example, it has been observed in plants that there often is variation in the level and pattern of transgene expression among individual events that differ in the chromosomal insertion site of the transgene but are otherwise identical. There may also be undesirable and/or desirable phenotypic or agronomic differences between events. Because of this, it is often necessary to produce and analyze a large number of individual plant transformation events in order to select an event having both the desirable trait and the optimal phenotypic and agricultural characteristics necessary to make it suitable for commercial purposes. Such selection often requires greenhouse and field trials with many events over multiple years, in multiple locations, and under a variety of conditions so that a significant amount of agronomic, phenotypic, and molecular data may be collected. The resulting data and observations must then be analyzed by teams of scientists and agronomists with the goal of selecting a commercially suitable event. Such an event, once selected, may then be used for introgressing the desirable trait into other genetic backgrounds using plant breeding methods, and thus producing a number of different crop varieties that contain the desirable trait and are suitably adapted to specific local growing conditions.

SUMMARY OF THE INVENTION

The invention provides transgenic cotton plants comprising event MON 88701, which exhibit commercially acceptable tolerance to applications of dicamba and glufosinate herbicides, having a representative seed sample deposited with the American Type Culture Collection (ATCC®) under Patent Deposit Designation PTA-11754. The invention also provides novel DNA molecules related to cotton event MON 88701 and methods of using these molecules. The invention also provides seeds, progeny, plant parts, cells, and commodity products of cotton plants comprising event MON 88701. The invention also provides methods of using cotton event MON 88701 and methods of producing cotton tolerant to both dicamba and glufosinate herbicides.

The invention provides recombinant DNA molecules related to cotton event MON 88701. These recombinant DNA molecules may comprise nucleotide molecules having a nucleotide sequence representing a region of the genomic DNA flanking the transgene insertion, and/or a region of the transgene insertion, and/or a contiguous sequence of any of these regions such as a region of the junction between the transgene insertion and flanking genomic DNA of cotton event MON 88701. The invention also provides DNA molecules useful as primers and probes diagnostic for cotton event MON 88701 and amplicons diagnostic for the presence of cotton event MON 88701. Cotton plants, plant cells, plant parts, commodity products, progeny, and seeds comprising these molecules are also disclosed.

The invention provides methods, compositions, and kits useful for detecting the presence and/or absence of DNA derived from cotton event MON 88701 and thus the presence and/or absence of the event. The invention provides a method for detection of MON 88701 by contacting a sample comprising DNA with a primer set that when used in a nucleic acid amplification reaction with genomic DNA from a cotton plant or seed comprising event MON 88701 produces an amplified DNA diagnostic for cotton event MON 88701, performing a nucleic acid amplification reaction thereby producing the amplified DNA, and detecting the presence and/or absence of the amplified DNA. The invention also provides a method for detection of MON 88701 by contacting a sample comprising DNA with a probe that when used in a hybridization reaction with DNA from cotton event MON 88701 hybridizes to a DNA molecule specific for cotton event MON 88701, performing a hybridization reaction, and detecting the hybridization of the probe to the DNA molecule. Kits comprising the methods and compositions of the invention useful for detecting the presence of DNA derived from cotton event MON 88701 are also provided.

The invention provides a cotton plant, seed, plant cell, progeny plant, plant part, or commodity product derived from a plant, plant cell, or seed comprising cotton event MON 88701. The invention also provides a cotton plant, seed, plant cell, progeny plant, plant part, or commodity product comprising a recombinant DNA molecule having a nucleotide sequence selected from the group consisting of SEQ ID NO: 1-10, and complements and fragments thereof. The invention also provides a cotton plant, seed, plant cell, progeny plant, plant part, or commodity product derived from the plant or seed comprising cotton event MON 88701 and comprising a recombinant DNA molecule that produces an amplified DNA molecule comprising a sequence selected from SEQ ID NO: 1-10 in a DNA amplification method.

The invention provides a method for controlling weeds in a field by planting cotton plants comprising event MON 88701 and then applying an effective dose of dicamba, glufosinate, or both dicamba and glufosinate herbicides capable of controlling the weeds without injuring the cotton event MON 88701 containing plants. The invention also provides a method for controlling weeds in a field by applying an effective dose of at least dicamba, glufosinate, or dicamba and glufosinate herbicides to control weeds in a field and then planting cotton plants comprising event MON 88701 in the field. The invention also provides a method for producing cotton seed or lint essentially free of weed seeds by planting seeds of a dicamba and glufosinate tolerant cotton plants comprising MON 88701 in a field, applying to the field a post-emergence effective dose of at least dicamba, glufosinate, or dicamba and glufosinate herbicides sufficient to kill the weed species, and harvesting seed or lint from the field.

The invention provides methods of producing a cotton plant and/or seed that tolerates application of dicamba and glufosinate herbicides by sexually crossing a cotton event MON 88701 containing plant comprising a sequence selected from SEQ ID NO: 1-10 with a second cotton plant, thereby producing seed, growing the seed to produce progeny plants, treating the progeny plants with dicamba and/or glufosinate, and selecting a progeny plant that is tolerant to both dicamba and glufosinate. The methods may also include selfing the selected progeny plant to produce a plurality of second generation progeny plants and selecting from these a dicamba and glufosinate tolerant plant. The methods may also include sexually crossing the selected progeny plant with another cotton plant to produce seed, growing the seed to produce a second generation of progeny plants, treating the second generation of progeny plants with dicamba and/or glufosinate, and selecting a second generation progeny plant that is tolerant to dicamba and glufosinate. The invention provides methods of producing a cotton plant and/or seed that tolerates application of dicamba and glufosinate herbicides by selfing a dicamba and glufosinate tolerant cotton plant comprising event MON 88701 comprising a sequence selected from SEQ ID NO: 1-10, thereby producing seed, growing the seed to produce progeny plants, treating the progeny plants with dicamba and/or glufosinate; and selecting a progeny plant that is tolerant to dicamba and glufosinate. The invention provides methods of determining the zygosity of a cotton event MON 88701 containing plant or seed comprising contacting a cotton DNA sample with a primer set comprising SEQ ID NO: 11, 12, and 14 and a probe set comprising SEQ ID NO: 13 and 15; then performing a nucleic acid amplification reaction with the sample, primer set, and probe set; then detecting in the nucleic acid amplification reaction a first fluorescent signal that is diagnostic for event MON 88701 and a second fluorescent signal different from the first fluorescent signal and that is diagnostic for native cotton genomic DNA corresponding to the location of insertion of the event MON 88701 transgene; and analyzing the presence and/or absence of the first fluorescent signal and the second fluorescent signal in the nucleic acid amplification reaction, wherein the presence of both fluorescent signals indicates the sample is heterozygous for event MON 88701 and the presence of only the first fluorescent signal indicates the sample is homozygous for event MON 88701. The invention also provides a cotton plant, seed, plant cell, or plant part comprising dicamba and glufosinate tolerance genes mapped on chromosome A08 at the map position of 19.3 cM and bordered by NG0207927 at the map position of 18.6 cM on left and by NG0207529 at the map position of 20.0 cM on right, and methods of using the same. The foregoing and other aspects of the invention will become more apparent from the following detailed description.

BRIEF DESCRIPTION OF THE SEQUENCES

Figure 1:
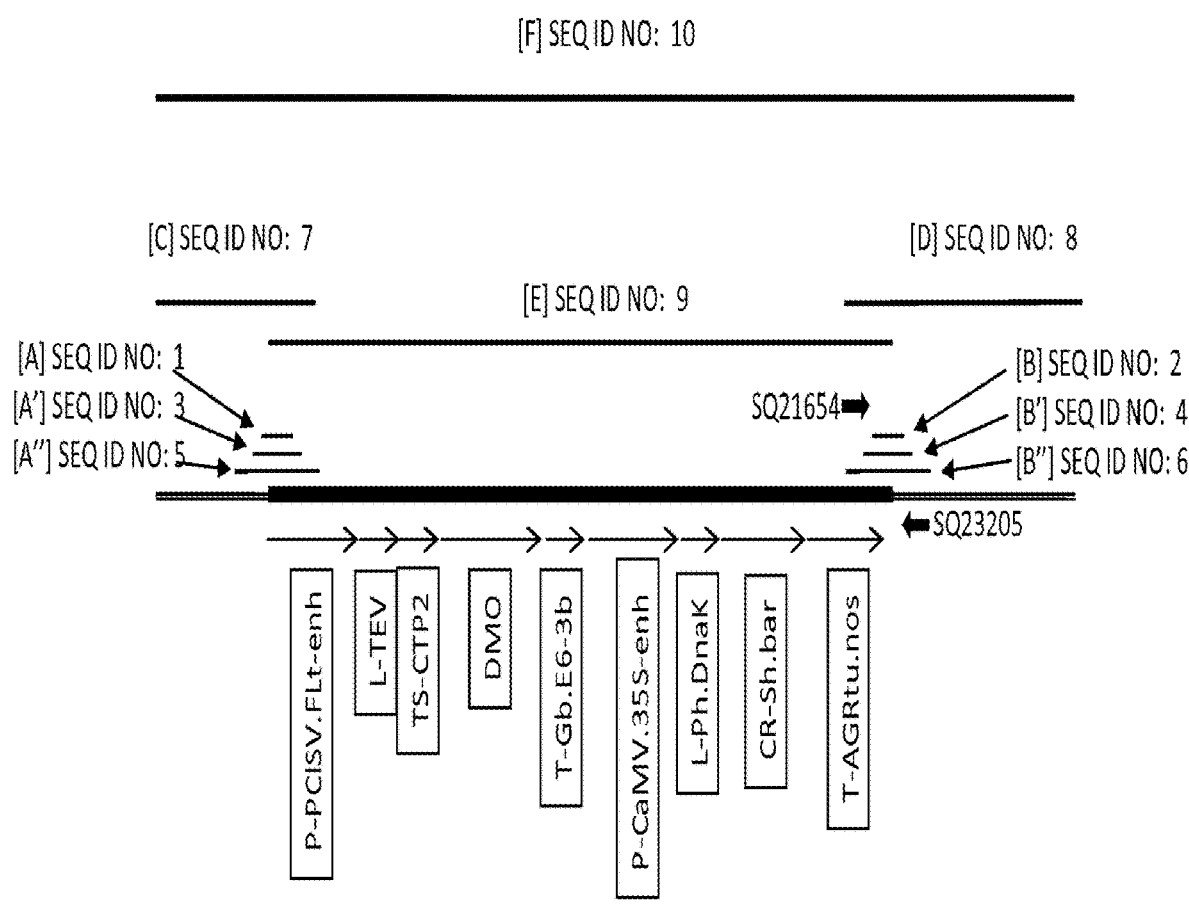
FIG. 1 illustrates the organization of the transgenic insert in the genome of a cotton plant comprising event MON 88701. [A] corresponds to the relative position of SEQ ID NO: 1; [A'] corresponds to the relative position of SEQ ID NO: 3; [A"] corresponds to the relative position of SEQ ID NO: 5; [B] corresponds to the relative position of SEQ ID NO: 2; [B'] corresponds to the relative position of SEQ ID NO: 4; [B"] corresponds to the relative position of SEQ ID NO: 6; [C] corresponds to the relative position of SEQ ID NO: 7; [D] corresponds to the relative position of SEQ ID NO: 8; [E] corresponds to the relative position of SEQ ID NO: 9; [F] corresponds to the relative position of SEQ ID NO: 10; SQ21654 and SQ23205 correspond to the relative position of primers used to identify cotton event MON 88701.

SEQ ID NO: 1 is a twenty nucleotide sequence representing the 5' junction region of cotton genomic DNA and the integrated transgenic expression cassette. SEQ ID NO: 1 is positioned in SEQ ID NO: 10 at nucleotide position 1117-1136.

SEQ ID NO: 2 is a twenty nucleotide sequence representing the 3' junction region of cotton genomic DNA and the integrated transgenic expression cassette. SEQ ID NO: 2 is positioned in SEQ ID NO: 10 at nucleotide position 5222-5241.

SEQ ID NO: 3 is a sixty nucleotide sequence representing the 5' junction region of cotton genomic DNA and the integrated transgenic expression cassette.

SEQ ID NO: 4 is a sixty nucleotide sequence representing the 3' junction region of cotton genomic DNA and the integrated transgenic expression cassette.

SEQ ID NO: 5 is a one-hundred nucleotide sequence representing the 5' junction region of cotton genomic DNA and the integrated transgenic expression cassette.

SEQ ID NO: 6 is a one-hundred nucleotide sequence representing the 3' junction region of cotton genomic DNA and the integrated transgenic expression cassette.

SEQ ID NO: 7 is the 5' sequence flanking the inserted DNA of MON 88701 up to and including a portion of integrated transgenic expression cassette.

SEQ ID NO: 8 is the 3' sequence flanking the inserted DNA of MON 88701 up to and including a portion of integrated transgenic expression cassette.

SEQ ID NO: 9 is the sequence of the integrated transgenic expression cassette.

SEQ ID NO: 10 is the contiguous nucleotide sequence of the 5' sequence flanking the inserted DNA (SEQ ID NO: 7), the integrated transgenic expression cassette (SEQ ID NO: 9), and the 3' sequence flanking the inserted DNA (SEQ ID NO: 8). SEQ ID NO: 10 includes SEQ ID NO: 1-9.

SEQ ID NO: 11 is the sequence of a primer referred to as Primer SQ21654 and used to identify cotton event MON 88701. It is complimentary to the inserted expression cassette at the region close to the 3' transgene insertion border. A PCR amplicon produced from a TAQMAN® (PE Applied Biosystems, Foster City, Calif.) assay using the combination of primers SQ21654 and SQ23205 (SEQ ID NO: 12) is a positive result for the presence of the event MON 88701. This primer set may also be used to identify a MON 88701 event in a zygosity assay.

SEQ ID NO: 12 is the sequence of a primer referred to as Primer SQ23205 and used to identify cotton event MON 88701. It is complimentary to a 3' region flanking the inserted expression cassette and close to the transgene DNA insertion border. A PCR amplicon produced from a TAQ-MAN® (PE Applied Biosystems, Foster City, Calif.) assay using the combination of primers SQ21654 (SEQ ID NO: 11) and SQ23205 is a positive result for the presence of the event MON 88701. This is also the primer used to identify MON 88701 event and wild-type with a zygosity assay.

SEQ ID NO: 13 is the sequence of a probe referred to as Probe PB10280 and used to identify cotton event MON 88701. It is complimentary to a region of the inserted expression cassette and adjacent to the 3' junction of the genomic DNA. This probe is a 6-FAM™-labeled synthetic oligonucleotide. Release of a fluorescent signal in an amplification reaction using primers SQ21654 and SQ23205 (SEQ ID NO: 11-12) in combination with 6-FAM™-labeled probe PB10280 is diagnostic of event MON 88701 in a TAQMAN® assay. PB10280 is also the probe used to identify a MON 88701 event in a zygosity assay.

SEQ ID NO: 14 is the sequence of a primer referred to as Primer SQ23901 and used to identify a cotton wild-type allele in a MON 88701 zygosity assay.

SEQ ID NO: 15 is the sequence of a VIC™-labeled probe referred to as Probe PB10631 and used to identify a cotton wild-type allele in a MON 88701 zygosity assay.

DETAILED DESCRIPTION

The following definitions and methods are provided to better define the invention and to guide those of ordinary skill in the art in the practice of the invention. Unless otherwise noted, terms are to be understood according to conventional usage by those of ordinary skill in the relevant art.

The invention provides a transgenic cotton event MON 88701 that exhibits commercially acceptable tolerance to applications of dicamba and glufosinate herbicides. The event comprises a single insertion of transgenic DNA into the chromosome/genome of the cotton germplasm. An "event" is produced by: (i) transformation of a plant cell with a nucleic acid construct that includes a transgene of interest, (ii) regeneration of a population of plants resulting from the insertion of the transgene into the genome of the plant, and (iii) selection of a particular plant characterized by insertion of the transgene into a particular location in the plant's genome.

The term "event" refers to a DNA molecule comprising the inserted DNA and the flanking cotton genomic DNA immediately adjacent to either side of the inserted DNA. This DNA molecule is created by the act of inserting the transgenic DNA into the genome of the cotton plant, i.e., by the act of transformation. This DNA molecule therefore comprises a nucleotide sequence that is both specific to the event and that is unique to the genome of the cotton plant into which the transgenic DNA has been inserted, in that this nucleotide sequence contains both the sequence of a particular region of cotton genomic DNA and of the transgenic DNA insert. The arrangement of the inserted DNA in cotton event MON 88701 in relation to the surrounding cotton plant genome DNA is therefore specific and unique for cotton event MON 88701. This DNA molecule is also an integral part of the cotton chromosome of event MON 88701 containing plants and as such is static in the plant and may be passed on to progeny of the plant.

The present invention also provides the original transformant that includes the transgene inserted into the particular location in the plant's genome and progeny of the transformant that include the transgene inserted into the particular location in the plant's genome. Such progeny may be produced by a sexual outcross between the transformant, or its progeny, and another plant. Such other plant may be a transgenic plant comprising the same or different transgene and/or a nontransgenic plant, such as one from a different variety. Even after repeated back-crossing to a recurrent parent, the inserted DNA and flanking DNA from the transformed parent is present in the progeny of the cross at the same genomic location.

As used herein, the term "cotton" means *Gossypium hirsutum* and includes all plant varieties that can be bred with cotton, including wild cotton species as well as those plants belonging to *Gossypium* that permit breeding between species.

Event MON 88701 comprises an integrated transgenic expression cassette that confers tolerance to applications of dicamba and glufosinate herbicides to the cotton plant. "Dicamba" refers to 3,6-dichloro-2-methoxybenzoic acid. Dicamba is a synthetic auxin herbicide useful for controlling broadleaf weeds. Cotton plants were transformed with a gene (dmo) from *Stenotrophomonas maltophilia* encoding dicamba mono-oxygenase (DMO). DMO is an enzyme that catalyzes the deactivation of dicamba via an O-demethylation reaction to the nonherbicidal compound 3,5-dichloro-salicylic acid. "Glufosinate" refers to 2-amino-4-(hydroxymethylphosphinyl)butanoic acid. Glufosinate is an organophosporus herbicide useful for controlling a broad spectrum of annual and perennial grass and broadleaf weeds. Cotton plants were transformed with a Bialaphos Resistance gene (bar) from *Streptomyces hygroscopicus* encoding phosphinothricin acetyl transferase (PAT). PAT is an enzyme that catalyzes acetylation and thus inactivation of glufosinate.

As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the cotton genomic DNA, which may ultimately result in the expression of a recombinant RNA and/or protein molecule in that organism. As used herein, a "recombinant plant" is a plant that would not normally exist in nature, is the result of human intervention, and contains a transgene and/or heterologous DNA molecule incorporated into its genome. As a result of such genomic alteration, the recombinant plant is distinctly different from the related wildtype plant. An example of a recombinant plant is a cotton plant described herein as comprising event MON 88701.

As used herein, the term "transgene" refers to a nucleotide molecule artificially incorporated into a host cell's genome. Such transgene may be heterologous to the host cell. The term "transgenic plant" refers to a plant comprising such a transgene.

As used herein, the term "heterologous" refers to a first molecule not normally found in combination with a second molecule in nature. For example, a molecule may be derived from a first species and inserted into the genome of a second species. The molecule would thus be heterologous to the host and artificially incorporated into a host cell's genome.

As used herein, the term "chimeric" refers to a single DNA molecule produced by fusing a first DNA molecule to a second DNA molecule, where neither first nor second DNA molecule would normally be found in that configuration, i.e., fused to the other. The chimeric DNA molecule is thus a new DNA molecule not otherwise normally found in nature.

The invention provides DNA molecules and their corresponding nucleotide sequences. As used herein, the term "DNA", "DNA molecule", "nucleotide molecule" refers to a DNA molecule of genomic or synthetic origin, i.e., a polymer of deoxyribonucleotide bases or a polynucleotide molecule, read from the 5' (upstream) end to the 3' (downstream) end. As used herein, the term "DNA sequence", "nucleotide sequence" or "polynucleotide sequence" refers to the nucleotide sequence of a DNA molecule. The nomenclature used herein is that required by Title 37 of the United States Code of Federal Regulations § 1.822 and set forth in the tables in WIPO Standard ST.25 (1998), Appendix 2, Tables 1 and 3. By convention, the nucleotide sequences of the invention provided as SEQ ID NOs: 1-10 and fragments thereof are disclosed with reference to only one strand of the two complementary nucleotide sequence strands. By implication, the complementary sequences (i.e. the sequences of the complementary strand), also referred to in the art as the reverse complementary sequences, are within the scope of the invention and are expressly intended to be within the scope of the subject matter claimed.

The nucleotide sequence corresponding to the complete nucleotide sequence of the inserted transgenic DNA and substantial segments of the cotton genome DNA flanking either end of the inserted transgenic DNA is provided herein as SEQ ID NO: 10. A subsection of this is the inserted transgenic DNA provided as SEQ ID NO: 9. The nucleotide sequence of the cotton genome DNA physically linked by phosphodiester bond linkage to and therefore flanking the 5' end of the inserted transgenic DNA is set forth as shown in FIG. 1 and provided as SEQ ID NO: 1, 3, 5, and 7. The nucleotide sequence of the cotton genome DNA physically linked by phosphodiester bond linkage to and therefore flanking the 3' end of the inserted transgenic DNA is set forth as shown in FIG. 1 and provided as SEQ ID NO: 2, 4, 6, and 8.

The cotton event MON 88701 further comprises two regions, one spanning the 5' location and one spanning the 3' location where the transgenic DNA is inserted into the genomic DNA, referred to herein as the 5' and 3' junction, respectively. A "junction sequence" or "junction region" refers to the DNA sequence and/or corresponding DNA molecule that spans the inserted transgenic DNA and the adjacent flanking genomic DNA. The junction sequences may be arbitrarily represented by the nucleotide sequences provided as SEQ ID NO: 1 and SEQ ID NO: 2, each representing 10 nucleotides of the flanking genomic DNA adjacent to and contiguous with 10 nucleotides of insert DNA. Alternatively, the junction sequences may be arbitrarily represented by the two 60 nucleotide sequences provided as SEQ ID NO: 3 and SEQ ID NO: 4, each representing 30 nucleotides of the flanking genomic DNA adjacent to and contiguous with 30 nucleotides of insert DNA. Alternatively, the junction sequences may be arbitrarily represented by the two 100 nucleotide sequences provided as SEQ ID NO: 5 and SEQ ID NO: 6, each representing 50 nucleotides of the flanking genomic DNA adjacent to and contiguous with 50 nucleotides of insert DNA. These nucleotides are connected by phosphodiester linkage and in cotton event MON 88701 are present as part of the genome. The identification of one or more of SEQ ID NO: 1-10 in a sample derived from a cotton plant, seed, or plant part is determinative that the DNA was obtained from cotton event MON 88701 and is diagnostic for the presence in a sample of DNA from cotton event MON 88701. The invention thus provides a DNA molecule that contains at least one of the nucleotide sequences provided as SEQ ID NO: 1-10. Any segment of DNA derived from transgenic cotton event MON 88701 that is sufficient to include at least one of the sequences provided as provided as SEQ ID NO: 1-10 is within the scope of the invention. In addition, any polynucleotide comprising a sequence complementary to any of the sequences described within this paragraph is within the scope of the invention. FIG. 1 illustrates the physical arrangement of SEQ ID NO: 1-9 relative to SEQ ID NO: 10 arranged from 5' to 3'.

The invention provides exemplary DNA molecules that can be used either as primers or probes for diagnosing the presence of DNA derived from a cotton plant comprising event MON 88701 in a sample. Such primers or probes are specific for a target nucleic acid sequence and as such are useful for the identification of cotton event MON 88701 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of cotton genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. An amplicon of the invention comprises at least one of the sequences provided as provided as SEQ ID NO: 1-10. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO: 11-12. The primer pair provided as SEQ ID NO: 11 and SEQ ID NO: 12 are useful as a first DNA molecule and a second DNA molecule that is different from the first DNA molecule, and both are each of sufficient length of contiguous nucleotides of SEQ ID NO: 10 to function as DNA primers that, when used together in a thermal amplification reaction with template DNA derived from cotton event MON 88701, to produce an amplicon diagnostic for cotton event MON 88701 DNA in a sample.

A "probe" is an isolated nucleic acid that is complementary to a strand of a target nucleic acid. Probes according to the invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. An exemplary DNA molecule useful as a probe is provided as SEQ ID NO: 13.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from cotton event MON 88701 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985). As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, two molecules exhibit "complete complementarity" if when aligned every nucleotide of the first molecule is complementary to every nucleotide of the second molecule. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

As used herein, the term "isolated" refers to at least partially separating a molecule from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying cotton event MON 88701, selecting plant varieties or hybrids comprising cotton event MON 88701, detecting the presence of DNA derived from the transgenic cotton event MON 88701 in a sample, and monitoring samples for the presence and/or absence of cotton event MON 88701 or plant parts derived from cotton plants comprising event MON 88701.

The invention provides cotton plants, progeny, seeds, plant cells, plant parts (such as pollen, ovule, pod, flower tissue, root tissue, stem tissue, and leaf tissue), and commodity products. These plants, progeny, seeds, plant cells, plant parts, and commodity products contain a detectable amount of a polynucleotide of the invention, i.e., such as a polynucleotide having at least one of the sequences provided as SEQ ID NO: 1-10. Plants, progeny, seeds, plant cells, and plant parts of the invention may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a cotton plant lacking such additional transgene.

The invention provides cotton plants, progeny, seeds, plant cells, and plant part such as pollen, ovule, pod, flower, root or stem tissue, and leaves derived from a transgenic cotton plant comprising event MON 88701. A representative sample of cotton seed comprising event MON 88701 has been deposited according to the Budapest Treaty with the American Type Culture Collection (ATCC®). The ATCC repository has assigned the Patent Deposit Designation PTA-11754 to the event MON 88701 comprising seed.

The invention provides a microorganism comprising a DNA molecule having at least one sequence selected from SEQ ID NO: 1-10 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event DNA, including the transgene, to progeny. As used herein, "progeny" includes any plant, seed, plant cell, and/or regenerable plant part comprising the event DNA derived from an ancestor plant and/or comprising a DNA molecule having at least one sequence selected from SEQ ID NO: 1-10. Plants, progeny, and seeds may be homozygous or heterozygous for the transgene. Progeny may be grown from seeds produced by a cotton event MON 88701 containing plant and/or from seeds produced by a plant fertilized with pollen from a cotton event MON 88701 containing plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another unrelated plant, to produce a varietal or a hybrid seed or plant. The other unrelated plant may be transgenic or nontransgenic. A varietal or hybrid seed or plant of the invention may thus be derived by crossing a first parent that lacks the specific and unique DNA of the cotton event MON 88701 with a second parent comprising cotton event MON 88701, resulting in a hybrid comprising the specific and unique DNA of the cotton event MON 88701. Each parent can be a hybrid or an inbred/varietal, so long as the cross or breeding results in a plant or seed of the invention, i.e., a seed having at least one allele containing the DNA of cotton event MON 88701 and/or a DNA molecule having at least one sequence selected from SEQ ID NO: 1-10. Two different transgenic plants may thus be crossed to produce hybrid offspring that contain two independently segregating, added, exogenous genes. For example, the MON 88701 containing dicamba and glufosinate tolerant cotton can be crossed with other transgenic cotton plants to produce a plant having the characteristics of both transgenic parents. One example of this would be a cross of MON 88701 containing dicamba and glufosinate tolerant cotton with a plant having one or more additional traits such as herbicide tolerance (e.g. cotton event MON 1445 or cotton event MON 88913) and/or insect control (e.g. cotton event MON 15985, MON 757, or MON 531), resulting in a progeny plant or seed that is tolerant to dicamba and glufosinate and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The invention provides a plant part that is derived from cotton plants comprising event MON 88701. As used herein, a "plant part" refers to any part of a plant which is comprised of material derived from a cotton plant comprising event MON 88701. Plant parts include but are not limited to pollen, ovule, pod, flower, root or stem tissue, fibers, and leaves. Plant parts may be viable, nonviable, regenerable, and/or nonregenerable.

The invention provides a commodity product that is derived from cotton plants comprising event MON 88701. As used herein, a "commodity product" refers to any composition or product which is comprised of material derived from a cotton event MON 88701 containing plant, seed, plant cell, or plant part. Commodity products may be sold to consumers and may be viable or nonviable. Nonviable commodity products include but are not limited to nonviable seeds; processed seeds, seed parts, and plant parts; lint; seeds and plant parts processed for feed or food, oil, fiber, paper, biomasses, and fuel products. Viable commodity products include but are not limited to seeds, plants, and plant cells. The cotton plants comprising event MON 88701 can thus be used to manufacture any commodity product typically acquired from cotton. Any such commodity product that is derived from cotton plants comprising event MON 88701 may contain at least a detectable amount of the specific and unique DNA corresponding to cotton event MON 88701, and specifically may contain a detectable amount of a polynucleotide comprising a DNA molecule having at least one sequence selected from SEQ ID NO: 1-10. Any standard method of detection for nucleotide molecules may be used, including methods of detection disclosed herein. A commodity product is within the scope of the invention if there is any detectable amount of a DNA molecule having at least one sequence selected from SEQ ID NO: 1-10 in the commodity product.

The plants, progeny, seeds, plant cells, plant parts (such as pollen, ovule, pod, flower, root or stem tissue, and leaves), and commodity products of the invention are therefore useful for, among other things, growing plants for the purpose of producing seed and/or plant parts comprising cotton event MON 88701 for agricultural purposes, producing progeny comprising cotton event MON 88701 for plant breeding and research purposes, use with microbiological techniques for industrial and research applications, and sale to consumers.

The invention provides methods for controlling weeds and methods for producing plants using dicamba and glufosinate herbicides and cotton event MON 88701. A method for controlling weeds in a field is provided and consists of planting cotton event MON 88701 containing varietal or hybrid plants in a field and applying a herbicidally effective dose of dicamba or glufosinate or dicamba and glufosinate to the field for the purpose of controlling weeds in the field without injuring the MON 88701 containing plants. Such application of dicamba or glufosinate or dicamba and glufosinate herbicides may be pre-emergence, i.e., any time after MON 88701 containing seed is planted and before MON 88701 containing plants emerge, or post-emergence, i.e., any time after MON 88701 containing plants emerge. Another method for controlling weeds in a field is also provided and consists of applying an effective dose of dicamba or glufosinate or dicamba and glufosinate herbicides to control weeds in a field and then planting cotton plants comprising event MON 88701 in the field. Such application of dicamba or glufosinate or dicamba and glufosinate herbicides would be pre-planting, i.e., before MON 88701 containing seed is planted, and could be done any time pre-planting including, but not limited to, about 14 days pre-planting to about 1 day pre-planting. The invention also provides a method for producing cotton seed or lint essentially free of weed seeds by planting seeds of a dicamba and glufosinate tolerant cotton plants comprising MON 88701 in a field, applying a post-emergence effective dose of dicamba or glufosinate or dicamba and glufosinate herbicides sufficient to kill the weed to the field, and harvesting seed or lint from the field. A herbicidally effective dose of dicamba for use in the field should consist of a range from about 0.005 pounds per acre to about 16 pounds per acre of dicamba over a growing season. In one embodiment, a total of about 0.5 pounds per acre to about 2 pounds per acre of dicamba is applied over a growing season. Multiple applications of dicamba may be used over a growing season, for example, two applications (such as a pre-planting application and a post-emergence application or a pre-emergence application and a post-emergence application) or three applications (such as a pre-planting application, a pre-emergence application, and a post-emergence application). A herbicidally effective dose of glufosinate for use in the field should consist of a range from about 0.005 pounds per acre to about 16 pounds per acre of glufosinate over a growing season. In one embodiment, a total of about 0.5 pounds per acre to about 1.59 pounds per acre of glufosinate is applied over a growing season. Multiple applications of glufosinate may be used over a growing season, for example, two applications (such as a pre-planting application and a post-emergence application or a pre-emergence application and a post-emergence application) or three applications (such as a pre-planting application, a pre-emergence application, and a post-emergence application or three post-emergence applications).

Methods for producing an herbicide tolerant cotton plant comprising the DNA sequences specific and unique to event MON 88701 of the invention are provided. Transgenic plants used in these methods may be homozygous or heterozygous for the transgene. Progeny plants produced by these methods may be varietal or hybrid plants; may be grown from seeds produced by a cotton event MON 88701 containing plant and/or from seeds produced by a plant fertilized with pollen from a cotton event MON 88701 containing plant; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

A cotton plant that tolerates application of dicamba and glufosinate herbicides may be produced by sexually crossing an event MON 88701 containing plant comprising a DNA molecule having at least one sequence selected from SEQ ID NO: 1-10 with another cotton plant and thereby producing seed, which is then grown into progeny plants. These progeny plants may then be treated with dicamba and/or glufosinate herbicides to select for progeny plants that are tolerant to dicamba and glufosinate herbicides. Alternatively, these progeny plants may be analyzed using diagnostic methods to select for progeny plants that contain the event MON 88701 DNA. The other plant used in the crossing may or may not be tolerant to dicamba and glufosinate herbicides and may or may not be transgenic. The progeny plant and/or seed produced may be varietal or hybrid seed. In practicing this method, the step of sexually crossing one plant with another plant, i.e., cross-pollinating, may be accomplished or facilitated by human intervention, for example: by human hands collecting the pollen of one plant and contacting this pollen with the style or stigma of a second plant; by human hands and/or actions removing, destroying, or covering the stamen or anthers of a plant (e.g., by detasseling or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma (e.g., in soy which naturally has flowers that hinder or prevent cross-pollination, making them naturally obligate self-pollinators without human intervention); by selective placement of plants (e.g., intentionally planting plants in pollinating proximity); and/or by application of chemicals to precipitate flowering or to foster receptivity (of the stigma for pollen).

A cotton plant that tolerates application of dicamba and glufosinate herbicides may be produced by selfing an event MON 88701 containing plant comprising a DNA molecule having at least one sequence selected from SEQ ID NO: 1-10 and thereby producing seed, which is then grown into progeny plants. These progeny plants may then be treated with dicamba and glufosinate herbicides to select for progeny plants that are tolerant to dicamba and glufosinate herbicides. Alternatively, these progeny plants may be analyzed using diagnostic methods to select for progeny plants that contain the event MON 88701 DNA. In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by detasseling or by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

Progeny cotton plants and seeds encompassed by these methods and produced by using these methods will be distinct from other cotton plants, for example because the progeny cotton plants and seeds: are recombinant and as such created by human intervention; are dicamba and glufosinate herbicide tolerant; contain at least one allele that consists of the transgene DNA of the invention; and/or contain a detectable amount of a DNA molecule comprising at least one sequence selected from SEQ ID NO: 1-10. A seed may be selected from an individual progeny plant, and so long as the seed comprises a DNA molecule having at least one sequence selected from SEQ ID NO: 1-10, it will be within the scope of the invention.

In practicing the invention, two different transgenic plants can be crossed to produce hybrid offspring that contain two independently segregating heterologous genes. Selfing of appropriate progeny can produce plants that are homozygous for both genes. Back-crossing to a parental plant and out-crossing with a non-transgenic plant are also contemplated, as is vegetative propagation. Descriptions of other methods that are commonly used for different traits and crops can be found in one of several references, e.g., Fehr, in Breeding Methods for Cultivar Development, Wilcox J. ed., American Society of Agronomy, Madison Wis. (1987).

The plants and seeds used in the methods disclosed herein may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a cotton plant lacking such additional transgene.

The methods of the invention are therefore useful for, among other things, controlling weeds in a field while growing plants for the purpose of producing seed and/or plant parts comprising cotton event MON 88701 for agricultural or research purposes, selecting for progeny comprising cotton event MON 88701 for plant breeding or research purposes, and producing progeny plants and seeds comprising cotton event MON 88701.

The plants, progeny, seeds, plant cells, plant parts (such as pollen, ovule, pod, flower, root or stem tissue, and leaves), and commodity products of the invention may be evaluated for DNA composition, gene expression, and/or protein expression. Such evaluation may be done by using any standard method such as PCR, northern blotting, southern analysis, western blotting, immuno-precipitation, and ELISA or by using the methods of detection and/or the detection kits provided herein.

Methods of detecting the presence of DNA derived from a cotton cell, tissue, seed, or plant comprising cotton event MON 88701 in a sample are provided. One method consists of (i) extracting a DNA sample from at least one cotton cell, tissue, seed, or plant, (ii) contacting the DNA sample with at least one primer that is capable of producing DNA sequence specific to event MON 88701 DNA under conditions appropriate for DNA sequencing, (iii) performing a DNA sequencing reaction, and then (iv) confirming that the nucleotide sequence comprises a nucleotide sequence specific for event MON 88701, such as one selected from the group consisting of SEQ ID NO: 1-10. Another method consists of (i) extracting a DNA sample from at least one cotton cell, tissue, seed, or plant, (ii) contacting the DNA sample with a primer pair that is capable of producing an amplicon from event MON 88701 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event MON 88701, such as one selected from the group consisting of SEQ ID NO: 1-10. The amplicon should be one that is specific for event MON 88701, such as an amplicon that comprises SEQ ID NO: 1 or SEQ ID NO: 2. The detection of a nucleotide sequence specific for event MON 88701 in the amplicon is determinative and/or diagnostic for the presence of the cotton event MON 88701 specific DNA in the sample. An example of a primer pair that is capable of producing an amplicon from event MON 88701 DNA under conditions appropriate for DNA amplification is provided as SEQ ID NO: 11-12. Other primer pairs may be readily designed by one of skill in the art and would comprise at least one fragment of SEQ ID NO: 10. Another method of detecting the presence of DNA derived from a cotton cell, tissue, seed, or plant comprising cotton event MON 88701 in a sample consists of (i) extracting a DNA sample from at least one cotton cell, tissue, seed, or plant, (ii) contacting the DNA sample with a DNA probe specific for event MON 88701 DNA, (iii) allowing the probe and the DNA sample to hybridize under stringent hybridization conditions, and then (iv) detecting hybridization between the probe and the target DNA sample. An example of the sequence a DNA probe that is specific for event MON 88701 DNA is provided as SEQ ID NO: 13. Other probes may be readily designed by one of skill in the art and would comprise at least one fragment of SEQ ID NO: 10. Detection of probe hybridization to the DNA sample is diagnostic for the presence of cotton event MON 88701 specific DNA in the sample. Absence of hybridization is alternatively diagnostic of the absence of cotton event MON 88701 specific DNA in the sample.

DNA detection kits are provided that are useful for the identification of cotton event MON 88701 DNA in a sample and can also be applied to methods for breeding cotton plants containing the appropriate event DNA. Such kits contain DNA primers and/or probes comprising fragments of SEQ ID NO: 1-10. One example of such a kit comprises at least one DNA molecule of sufficient length of contiguous nucleotides of SEQ ID NO: 10 to function as a DNA probe useful for detecting the presence and/or absence of DNA derived from transgenic cotton plants comprising event MON 88701 in a sample. The DNA derived from transgenic cotton plants comprising event MON 88701 would comprise a DNA molecule having at least one sequence selected from SEQ ID NO: 1-10. A DNA molecule sufficient for use as a DNA probe is provided that is useful for determining, detecting, or diagnosing the presence and/or absence of cotton event MON 88701 DNA in a sample is provided as SEQ ID NO: 13. Other probes may be readily designed by one of skill in the art and should comprise at least 15 contiguous nucleotides of SEQ ID NO: 10 and be sufficiently unique to cotton event MON 88701 DNA in order to identify DNA derived from the event. Another type of kit comprises a primer pair useful for producing an amplicon useful for detecting the presence and/or absence of DNA derived from transgenic cotton event MON 88701 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO: 1-10, and then detecting the presence and/or absence of the amplicon. Such a method may also include sequencing the amplicon or a fragment thereof, which would be determinative of, i.e. diagnostic for, the presence of the cotton event MON 88701 specific DNA in the target DNA sample. Other primer pairs may be readily designed by one of skill in the art and should comprise at least 15 contiguous nucleotides of SEQ ID NO: 10 and be sufficiently unique to cotton event MON 88701 DNA in order to identify DNA derived from the event.

Nucleic-acid amplification can be accomplished by any of the various nucleic-acid amplification methods known in the art, including thermal amplification methods. Many techniques are known in the art for detecting, quantifying, and/or sequencing the amplicon produced by these methods. One exemplary technique useful in practicing this invention is TAQMAN® (PE Applied Biosystems, Foster City, Calif.).

The kits and detection methods of the invention are useful for, among other things, identifying cotton event MON 88701, selecting plant varieties or hybrids comprising cotton event MON 88701, detecting the presence of DNA derived from the transgenic cotton plants comprising event MON 88701 in a sample, and monitoring samples for the presence and/or absence of cotton plants comprising event MON 88701 or plant parts derived from cotton plants comprising event MON 88701.

The sequence of the heterologous DNA insert, junction sequences, or flanking sequences from cotton event MON 88701 can be verified (and corrected if necessary) by amplifying such sequences from the event using primers derived from the sequences provided herein followed by standard DNA sequencing of the amplicon or of the cloned DNA.

As used herein, the term "comprising" means "including but not limited to".

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1: Transformation of Cotton and MON 88701 Event Selection

This example describes the production, analysis, and selection of event MON 88701. Summarized is the production and analysis of thousands of individual plants over multiple years through the rigorous molecular, phenotypic, and field testing required for the ultimate selection of the commercial event, the MON 88701 event.

The transgenic dicamba and glufosinate tolerant cotton event MON 88701 was created through *Agrobacterium*-mediated transformation of cotton hypocotyl tissue utilizing a plant transformation vector comprising the expression cassette illustrated in FIG. 1. Methods for transforming cotton are known in the art. To produce the MON 88701 event, Coker 130 cotton material (Asgrow, St Louis, Mo.) was used for plant transformation. Cotton cells were transformed and regenerated into intact cotton plants. Rooted plants with normal phenotypic characteristics were selected and transferred to soil for growth and further assessment.

R0 plants were transferred to soil and subjected to herbicide screening at 1× or 2× field rates (i.e., 0.5 or 1.0 lb/acre active ingredient) of both dicamba and glufosinate. Subsequently, R0 plants containing only a single T-DNA expression cassette were identified and selected. The T-DNA expression cassette contains the Peanut chlorotic streak virus (PClSV) promoter with a duplicated enhancer region (P-PClSV.FLt-enh); operably linked to a DNA leader derived from RNA transcript of Tobacco etch virus (L-TEV); operably linked to a DNA molecule encoding an N-terminal chloroplast transit peptide from chloroplast transit peptide from 5-enolpyruvylshikimate-3-phosphate synthase (EPSPS) from *Arabidopsis thaliana* (TS-CTP2); operably linked to a DNA molecule encoding dicamba monooxygenase (DMO) from *Stenotrophomonas maltophilia*; operably linked to a 3' UTR DNA molecule derived from the fiber protein E6 gene of sea-island cotton (T-Gb.E6-3b); operably linked to the promoter of the enhanced 35S RNA transcript (with a duplicated enhancer region) from Cauliflower mosaic virus (P-CaMV.35S-enh); operably linked to a DNA leader derived from the 5 untranslated region of the heat shock protein 70 (HSP70) gene from *Petunia x hybrida* (L-Ph.DnaK); operably linked to the Bialaphos Resistance gene (bar) gene from *Streptomyces hygroscopicus* encoding a phosphinothricin acetyl transferase (PAT) (CR-Sh.bar); operably linked to a 3' untranslated region from the nopaline synthase (NOS) gene (which directs polyadenylation of mRNA) from *Agrobacterium tumefaciens* (T-AGRtu.nos).

The MON 88701 event was selected from among approximately 151 individual transgenic events based on its superior combination of phenotypic characteristics (including commercial level tolerance to both dicamba and glufosinate herbicides), molecular characteristics (determined using a comprehensive molecular profile analysis), and haplotype association. Selection of the MON 88701 event from among the original 151 transgenic events was a multi-year process requiring data analysis at each step. Two waves of transformation events were processed to allow for a larger number of events from which to choose the final commercial event. Table 1 provides a summary of each type of analysis with the number of events selected and advanced for each step of event screening. The Puerto Rico field trial efficacy screen for Wave 2 preceded the first U.S. field trial.

TABLE 1

| Event Screening Analysis Step | Wave 1 | Wave 2 |
|---|---|---|
| R0 - Transformation Quality Analysis | 48 | 103 |
| R0 - Herbicide Efficacy Analysis | 26 | 57 |
| R1 - Agronomic Seed Production | 9 | 26 |
| R1 - Herbicide Efficacy Analysis | 9 | 23 |
| First U.S. Field Trial | 8 | 10 |
| Preliminary Molecular Analysis | 4 | 19 |
| Puerto Rico Field Trial Efficacy Screen | 3 | 17 |
| Second U.S. Field Trial | 2 | n/d |
| Detailed Molecular Analysis | 1 | 6 |

The original 151 transgenic R0 events were analyzed using a combination of analytical techniques (Transformation Quality Analysis including TaqMan and/or PCR analysis) and R0 Herbicide Efficacy Analysis (herbicide spray). Selected R0 event containing plants were then self-fertilized to produce R1 seed, and 32 of the events were then advanced for R1 Herbicide Efficacy Analysis.

Detailed molecular analysis was completed on events passing agronomic and efficacy field trials. Northern blots were used to confirm that the dmo and bar messenger RNA transcripts were present in samples prepared from seed of the tested events. Western blot analysis was done to confirm that a single DMO and PAT protein band was present in samples prepared from leaf tissue of the tested events. N-terminal sequencing of the isolated, purified PAT protein showed the expected amino acid sequence at the N-terminus of the PAT protein. N-terminal sequencing of the isolated, purified DMO protein showed 9 amino acids from the CTP (TS-CTP2) present at the N-terminus of the DMO protein.

Figure 2:
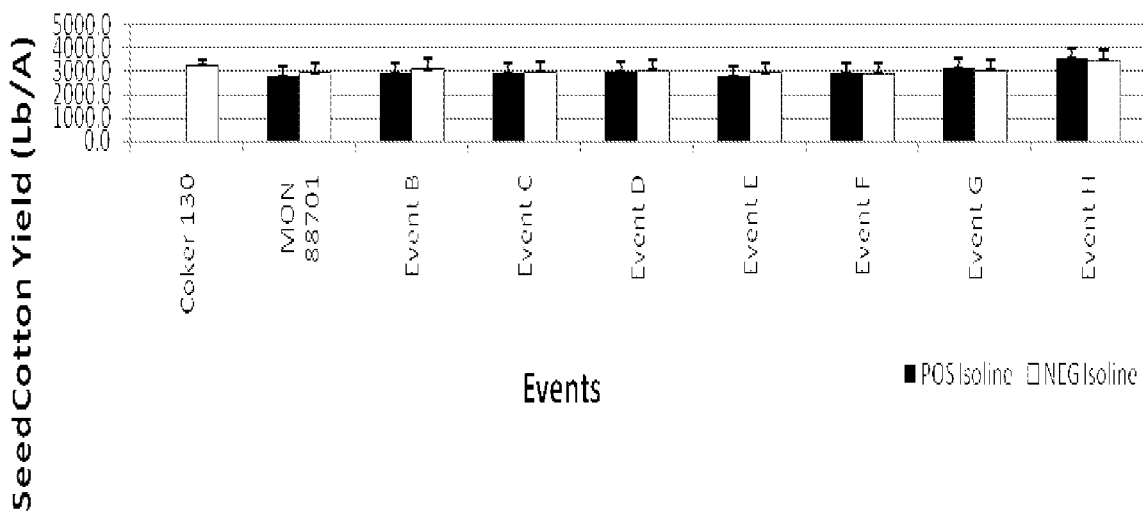
FIG. 2 shows two years of agronomic yield field trial data reported as pounds of seedcotton per acre.
Figure 2:
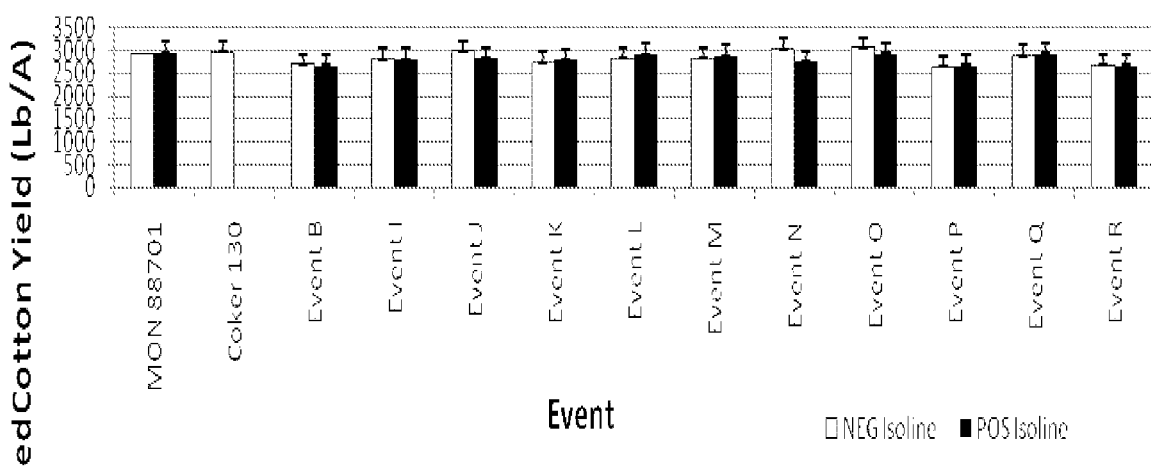

Agronomic field testing consisted of planting paired positive isoline and negative isoline events (containing the transgene cassette and lacking the transgene cassette, respectively) side-by-side with two rows of wild type (non-transgenic) Coker 130 per plot. The plots were maintained weed and insect free using conventional control programs for the duration of the trial. Data collected included planting date, stand counts, plant height, node number, gross agronomic/phenotypic differences, boll samples, harvest date, and yield. Stand counts for each plot were taken at 10 days after planting (DAP) and again at 20 DAP. Cotyledons that had completely cleared the soil were considered "emerged". Any differences noted in plant density, i.e. skips, poor germination, loss due to crusting, washouts, etc., were noted. Final stands had 10 plants per meter on average. Plant height measurements were taken at first flower plus two weeks (FF2). Average measurements of plant height (cm) of five plants per plot were recorded. On the same plants used for plant height measurements, the number of nodes were counted (cotyledon is node 0). Any gross agronomic differences were recorded, such as leaf morphology, branching habit, leaf color, time to flowering, fruiting pattern, etc. Boll samples were randomly harvested from 50 first position bolls (seedcotton only) from the middle of the plants (notes 8-12). The boll samples were used to calculate lint fraction and fiber quality. For yield determinations, plots were defoliated and a boll opener (with ethephon, i.e. PREP) was used prior to harvest. Plots were harvested and recorded as pounds per plot of seedcotton and expressed as pounds per acre of seedcotton. There was no significant yield difference between positive isoline events, the paired negative isoline events, and wild-type Coker 130 cotton for two years of agronomic field trials (FIG. 2).

Figure 3:
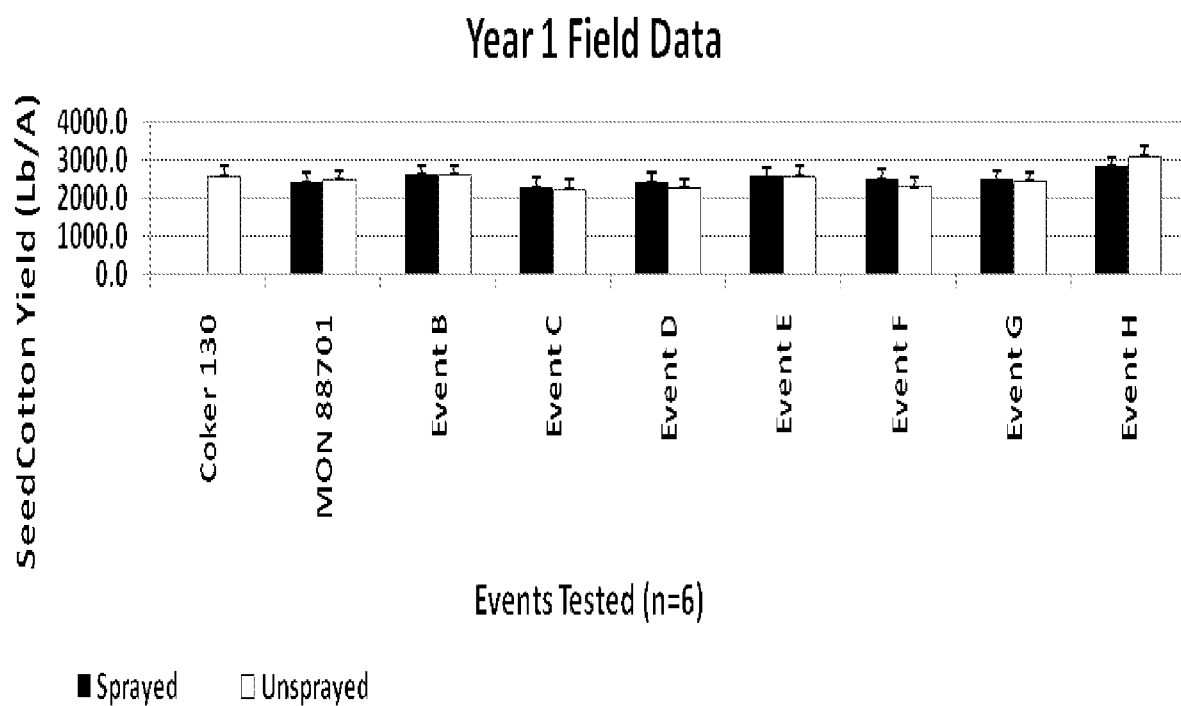
FIG. 3 shows first year yield field trial data reported as pounds of seedcotton per acre.
Figure 7:
FIG. 7 shows plants comprising event MON 88701 versus nontransgenic Coker 130 plants sprayed with dicamba and glufosinate in the field. Herbicide applications were 1 lb dicamba (2×) at pre; 1 lb glufosinate (2×) at 2-leaf; 1 lb dicamba at 5-leaf; and 1 lb glufosinate at 8 leaf.

In year 1, efficacy testing was conducted with eight events compared to non-transgenic, wild-type Coker 130. For this testing, paired plots were sprayed with dicamba (Clarity®, BASF, Research Triangle Park, N.C.) and glufosinate (Ignite®, Bayer CropScience, Research Triangle Park, N.C.) or left unsprayed. The plots were maintained weed- and insect-free using conventional control programs for the duration of the trial. All herbicide treatments are represented as pounds of active ingredient per acre (lb/A). For plots that were sprayed, the following applications were conducted: dicamba was applied preemergence at 1 lb/A followed by glufosinate applied 1.09 lb/A at the 2 node stage, followed by dicamba applied at 1 lb/A at the 5 node stage, followed by glufosinate applied 1.09 lb/A at the 8 node stage, followed by dicamba applied at 1 lb/A at the 12 node stage. Neither dicamba nor glufosinate were applied with surfactants, fertilizer additive, or other adjuvant. Injury ratings were taken at the following stages, which were immediately prior to the next assigned herbicide application: at the 2-node cotton stage, rating activity was taken for percent epinasty (dicamba damage) and percent total injury, with focus on epinasty; at the 5-node stage, rating activity was taken for percent epinasty, percent burn or necrosis (glufosinate injury) and percent total injury, with focus on necrosis; at the 8-node stage, rating activity was taken for percent epinasty, percent burn or necrosis, and percent total injury, with focus on epinasty; at the 12-node stage, rating activity was taken for percent epinasty, percent burn or necrosis and percent total injury, with focus on necrosis; at mid-bloom stage, rating activity was taken for percent epinasty, percent burn or necrosis and percent total injury, with focus on epinasty; and for late bloom stage, rating activity was taken for percent epinasty, percent burn or necrosis and percent total injury. Additional agronomic data were collected in these efficacy field trials including: planting date, stand counts (taken at 7 and 14 DAP), gross agronomic/phenotypic differences, harvest date, and yield. Injury ratings used standard weed science percent scales where 0% equals no crop injury and 100% equals complete crop death. Ratings made for dicamba injury are referred to as epinasty and appears as twisting, growth malformation. Ratings made for glufosinate injury are referred to as burn or necrosis and appears as chlorosis and or necrosis. For yield determinations, plots were defoliated and a boll opener (with ethephon, i.e. PREP) was used prior to harvest. Plots were harvested and yield recorded as lbs/plot of seed cotton and expressed as lb/acre of seed cotton. Agronomic/phenotypic differences were notedin fruiting profile as normal or as unusual. There was no significant difference in yield of seed cotton between paired sprayed and unsprayed events compared to unsprayed wild-type Coker 130 (FIG. 3). The wild-type Coker 130 did not survive the spray regimen (FIG. 7).

In year 2, efficacy testing was conducted with twelve events compared to non-transgenic, wild-type Coker 130. For this testing, paired plots were either sprayed or not sprayed. The plots were maintained weed- and insect-free using conventional control programs for the duration of the trial. For the plots that were sprayed, the following treatment applications were conducted (1) 0.5 lb/A dicamba applied PRE, Early POST, Mid POST and Late POST; (2) 1 lb/A dicamba applied PRE, Early POST, Mid POST and Late POST; (3) 2 lb/A dicamba applied PRE, Early POST, Mid POST and Late POST; (4) 0.5 lb/A glufosinate applied Early POST, Mid POST and Late POST: (5) 1 lb/A glufosinate applied Early POST, Mid POST and Late POST: 6) 2 lb/A glufosinate applied Early POST, Mid POST and Late POST; and 7) Control (unsprayed). Preemergence (PRE) is defined as immediately after cotton planting (within 24 hours); Early POST as 2-node cotton; Mid POST as 8-node cotton; and Late POST as 14 node cotton. For these efficacy field trials, there were three plots composed entirely of wild-type cotton (Coker 130). At each post-emergence timing (Early, Mid, Late), one-half of a plot was sprayed with the 1× rate (0.5 lb/A) of dicamba and one-half of the same plot was sprayed with the 1× rate (0.5 lb/A) of glufosinate. Each of the three plots received dicamba and glufosinate spray at one of the post-emergence timing spray applications (Early, Mid, Late).

The spray protocol consisted of the herbicides applied at 10 gallons per acre water volume using the following sprayer set up (which is within the standards used for most weed science research). XR TeeJet® extended range flat spray tips with an 80-degree spray angle were used (TeeJet Technologies, Wheaton, Ill.). There were 2 nozzles per row (nozzles spaced at 15" for 30" rows, 19" for 38" rows and 20" for 40" rows). Nozzle size depended on sprayer speed and nozzle spacing; however, nozzle size was selected to result in a spray pressure of 25 to 35 PSI. Boom height was adjusted to allow for 50% spray overlap (which occurs at roughly 30" above the top of the crop).

Figure 4:
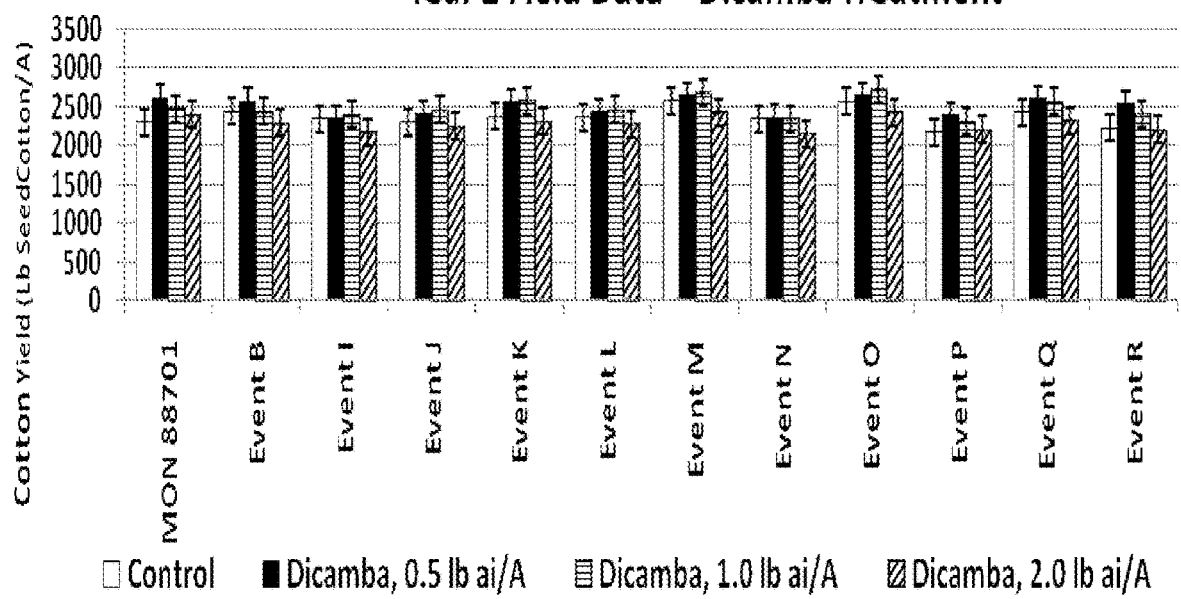
FIG. 4 shows second year yield field trial data reported as pounds of seedcotton per acre with increasing amounts of either dicamba (4.A.) or glufosinate (4.B.) herbicide.
Figure 4:
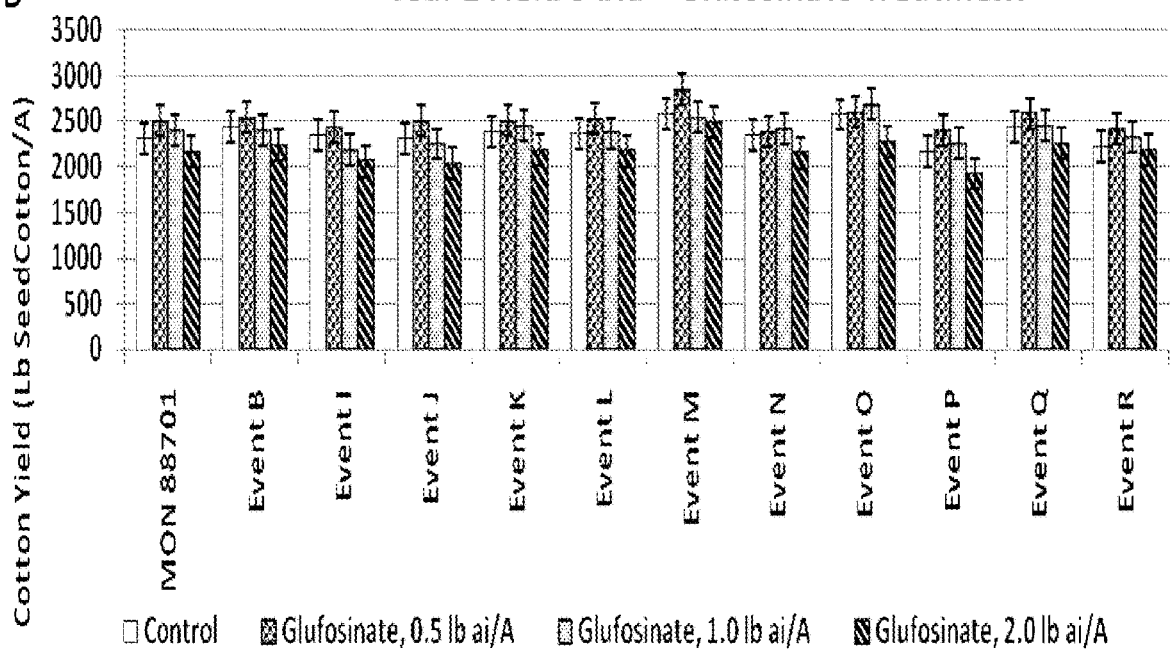
Figure 5:
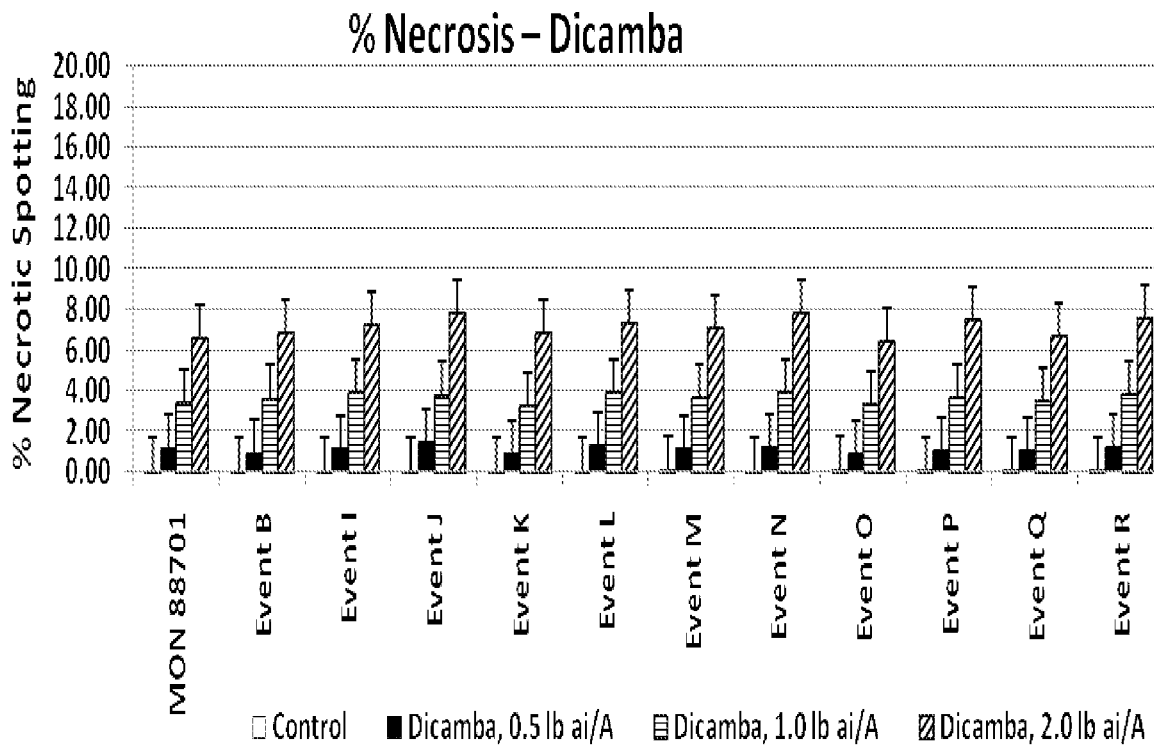
FIG. 5 shows percentage of necrotic spotting occurring with increasing amounts of either dicamba (5.A.) or glufosinate (5.B.) herbicide.
Figure 5:
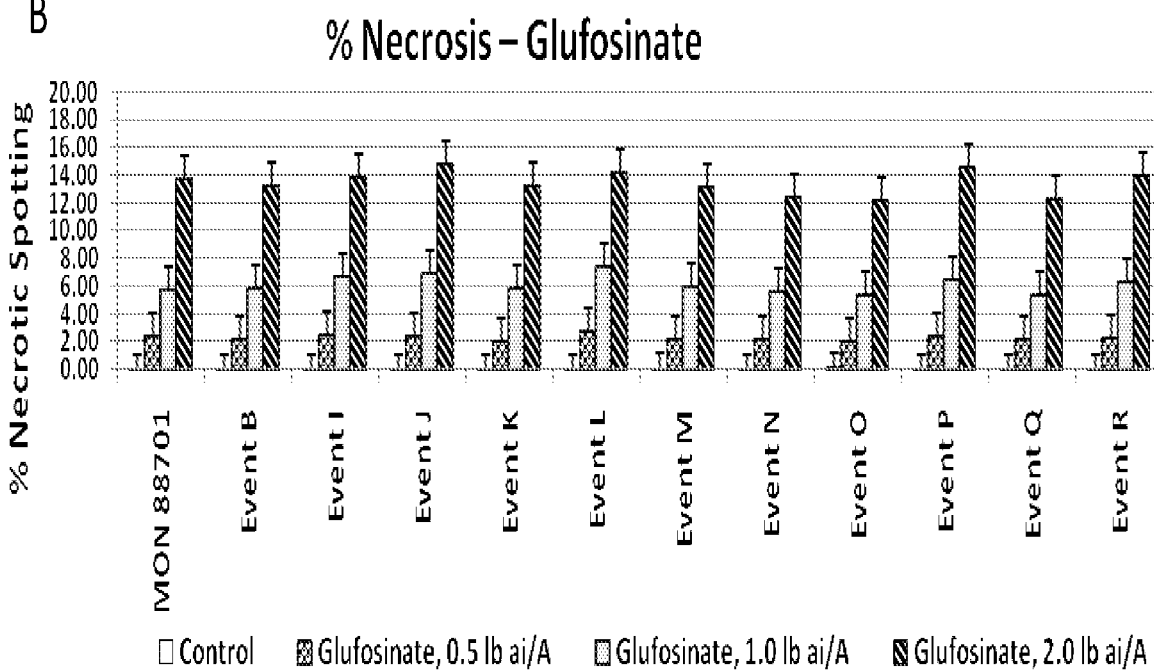

At each rating time, the following observations were recorded: 1) percent necrosis or burn on the most affected leaves; 2) percent necrosis or burn on a whole-plant basis; 3) epinasty; and 4) any other relevant injury that was observed. Ratings were taken four days after each application and immediately prior to subsequent applications. The rating schedule time and objective were as follows: 1) 4-7 days after emergence and again immediately before 2-node spray to check for preemergence effects of dicamba spray; 2) 4 days after the 2-node spray and again immediately before the 8-node spray to determine the rating of the 2-node spray; 3); 4 days after the 8-node spray and again immediately before the 14-node spray to determine the rating of the 8-node spray 4); 4 days after the 14-node spray and again 10 days after the 14-node spray to determine the rating of the 14-node spray; and 5) at cutout to determine the late season rating of the net effect of all sprays. Injury ratings used standard weed science percent scales where 0% equals no crop injury and 100% equals complete crop death. Ratings made for dicamba injury are referred to as epinasty and appears as twisting, growth malformation. Ratings made for glufosinate injury are referred to as burn or necrosis and appears as chlorosis and or necrosis. For yield determinations, plots were defoliated and a boll opener (with ethephon, i.e. PREP) was used prior to harvest. Plots were harvested and recorded as lbs/plot of seedcotton and expressed as lb/acre of seedcotton. Wild-type Coker 130 plants did not survive herbicide spray and therefore no yield was recorded from Coker 130 plots. As seen in FIG. 4.A, yield was nearly equivalent for plants comprising the MON 88701 event with increasing application rates of dicamba herbicide. As seen in FIG. 4.B, yield was nearly equivalent for plants comprising the MON 88701 event with increasing application rates of glufosinate herbicide. For injury ratings, FIG. 5.A shows increased percentage of injury to plants comprising the MON 88701 event with increasing application rates of dicamba. FIG. 5.B shows increased percentage of injury to plants comprising the MON 88701 event with increasing application rates of glufosinate.

In year 3, efficacy field testing of event MON 88701 was conducted to study the rate and timing of application of dicamba and/or glufosinate. The plots were maintained weed- and insect-free using conventional control programs for the duration of the trial. The treatment and application timing are detailed in Table 2. Neither dicamba nor glufosinate were applied with surfactants, fertilizer additive or other adjuvant. The sprayer protocol was as described for year 2 efficacy field testing. Stand rating, visual injury rating (percent epinasty, percent necrosis), plant height and node number, 50-boll sampling, and yield determinations were as described for agronomic and efficacy field testing above.

TABLE 2

| Treatment | Rate (lb ai/A) | Application timing | | | |
|---|---|---|---|---|---|
| | | 1 to 3 Node | 5 to 7 node | 10 to 12 node | 15 to 18 node |
| 1 | 0.5 | Dicamba | Glufosinate | Dicamba | Glufosinate |
| 2 | 1 | Dicamba | Glufosinate | Dicamba | Glufosinate |
| 3 | 0.5 | Glufosinate | Dicamba | Glufosinate | Dicamba |
| 4 | 1 | Glufosinate | Dicamba | Glufosinate | Dicamba |
| 5 | 0.25* | Tank Mix | Tank Mix | Tank Mix | Tank Mix |
| 6 | 0.5* | Tank Mix | Tank Mix | Tank Mix | Tank Mix |
| 7 | 1* | Tank Mix | Tank Mix | Tank Mix | Tank Mix |
| 8 | 0.5 | Dicamba | Dicamba | Dicamba | Dicamba |
| 9 | 1 | Dicamba | Dicamba | Dicamba | Dicamba |
| 10 | 0.5 | Glufosinate | Glufosinate | Glufosinate | Glufosinate |
| 11 | 1 | Glufosinate | Glufosinate | Glufosinate | Glufosinate |
| 12 | — | Control | — | — | — |

Figure 6:
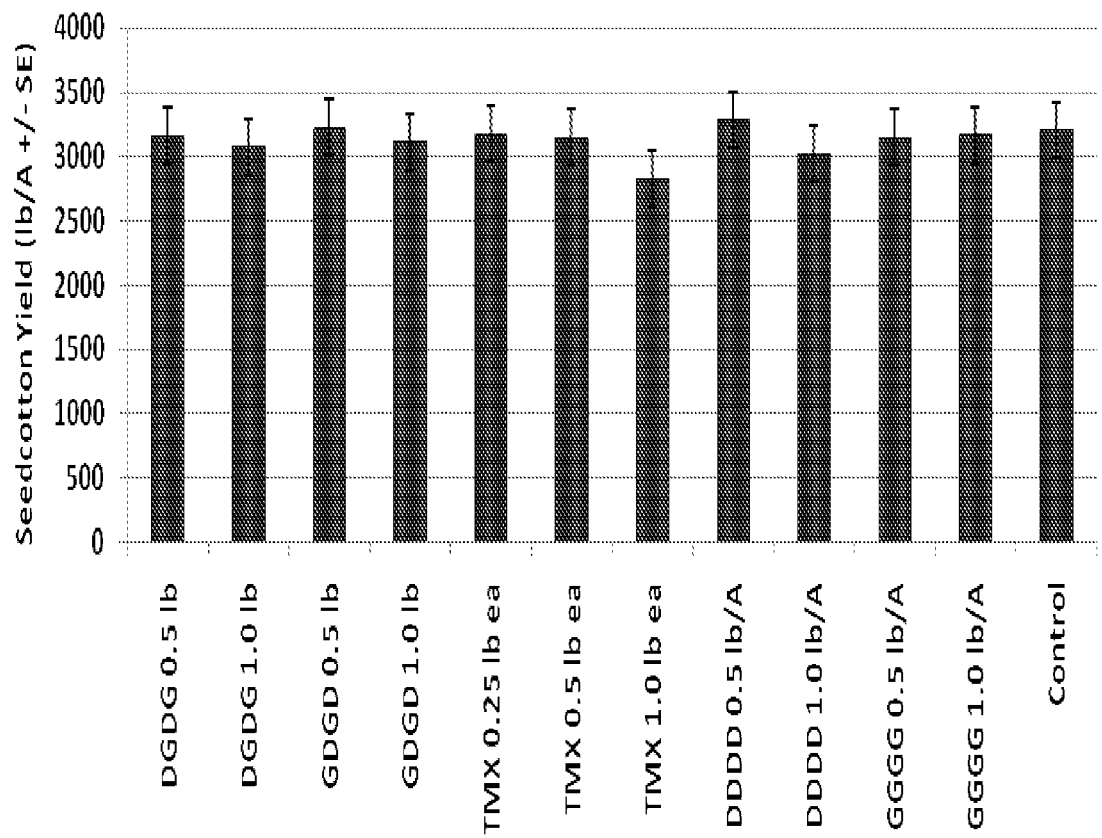
FIG. 6 shows yield field trial data as pounds of seedcotton per acre of the spray regimen for event MON 88701.

*With tank mixes, the rate is what was used for the individual herbicides: 0.25 = 0.25 lb/A dicamba + 0.25 lb/A glufosinate There was a slight yield drag when dicamba and glufosinate were tank mixed and applied at four times in season at 1 lb/acre each (FIG. 6). For all other treatment regimens, there was no yield loss to plants comprising the MON 88701 event when sprayed with dicamba, glufosinate, or dicamba and glufosinate (FIG. 6).

Example 2: Characterization of MON 88701 DNA Sequences

This example describes the molecular characterization of the MON 88701 event. The DNA inserted into the genome of cotton plants comprising MON 88701 and the genomic sequence flanking this insertion were characterized by detailed molecular analyses. These analyses included: the insert sequence, the insert number (number of integration sites within the cotton genome), the copy number (number of copies of transgene DNA within one locus), the integrity of the inserted gene cassette, the flanking sequences, and the association of the insertion with haplotype regions of the cotton genome.

Molecular DNA probes were used that included the intact coding region and its respective regulatory elements, the promoters, introns, and polyadenylation sequences of the plant expression cassettes. The analysis showed that MON 88701 contains a single transgene DNA insertion with one copy of the expression cassette. Inverse PCR and DNA sequence analyses were performed to determine the 5' and 3' insert-to-plant genome junctions, confirm the organization of the elements within the insert (FIG. 1), and determine the complete DNA sequence of the insert in cotton plants comprising event MON 88701 (provided herein as SEQ ID NO: 9). A cotton plant that comprises in its genome the linked transgene genetic elements shown in FIG. 1 and is resistant to dicamba and glufosinate herbicides is an aspect of the invention.

Sequences flanking the transgene DNA insertion in MON 88701 were determined using inverse PCR as described in Ochman et al., 1990 (PCR Protocols: A guide to Methods and Applications, Academic Press, Inc.) and/or genome walker techniques. Plant genomic DNA was isolated from both Coker 130 and the transgenic cotton lines from tissue grown under standard greenhouse conditions. Approximately 0.2 gram of young leaf tissue was lyophilized and powdered via the addition of several small steel beads followed by vigorous agitation. Tissue was washed twice with 5 mL of 100% methanol followed by one wash with 5 mL of 50% methanol to remove interfering phenolic compounds. DNA was extracted by the addition of 7 mL of CTAB extraction buffer (100 mM Tris pH 8.0, 1.4 M NaCl, 20 mM EDTA, 2% w/v hexadecyltrimethylammonium bromide, 1% w/v polyvinylpyrrolidone, 1% w/v poly(vinylpolypyrrolidone), 0.07% beta-mercaptoethanol, 1 mM DTT). Samples were incubated at 65° C. for 45 min to fully lyse cells then, spun for 5 min at 3000 g to remove insoluble debris. The supernatant was extracted with 7 mL of chloroform isoamyl alcohol 24:1, spun at 3000 g for 5 min to separate phases, and DNA was extracted from the aqueous phase in a fresh tube by the addition of 6 mL of isopropanol. DNA pellets were washed with 6 mL of 70% ethanol to remove any salts, and pellets were allowed to air dry. The DNA pellets were resuspended in 10 mM Tris pH 8.0 containing 0.5 ug/mL DNase-free RNase and incubated at 37° C. 1 hour. Following treatment, DNA was quantified using Quant-iT™ PicoGreen® (Molecular Probes, Inc. Eugene, Oreg.). This method can be modified by one skilled in the art to extract DNA from any tissue of cotton. An aliquot of DNA was digested with restriction endonucleases selected based upon restriction analysis of the transgene DNA. After self-ligation of restriction fragments, PCR was performed using primers designed from the transgene DNA sequence that would amplify sequences extending away from the 5' and 3' ends of the transgene DNA. PCR products were separated by agarose gel electrophoresis and purified using a QIAGEN gel purification kit (Qiagen, Valencia, Calif.). The subsequent DNA products were sequenced directly using standard DNA sequencing protocols. The 5' flanking sequence which extends into the right border sequence of the expression cassette transgene DNA is presented as SEQ ID NO: 7 ([C], see FIG. 1). The 3' flanking sequence which extends into the left border sequence of the expression cassette transgene DNA is presented as SEQ ID NO: 8 ([D], see FIG. 1). The portion of the expression cassette DNA that was fully integrated into the Coker genomic DNA is presented as SEQ ID NO: 9 ([E], see FIG. 1).

Isolated DNA molecule sequences were compared to the transgene DNA sequence to identify the flanking sequence and the co-isolated transgene DNA fragment. Confirmation of the presence of the expression cassette was achieved by PCR with primers designed based upon the deduced flanking sequence data and the known transgene DNA sequence. The wild-type sequence corresponding to the same region in which the transgene DNA was integrated in the transformed line was isolated using primers designed from the flanking sequences in MON 88701. The PCR reactions were performed using the Phusion® High-Fidelity PCR Master Mix with HF Buffer (New England Biolabs, Ipswich, Mass.). The flanking DNA sequences in MON 88701 and the Coker wild-type sequence were analyzed against multiple nucleotide and protein databases. This information was used to examine the relationship of the transgene to the plant genome and to look for the insertion site integrity. The flanking sequence and wild-type sequences were used to design primers for TAQMAN® endpoint assays used to identify the events. Zygosity assays were developed using this information.

The dicamba and glufosinate tolerance transgene cassette was mapped in cotton plants comprising event MON 88701 on chromosome A08 at the map position of 19.3 cM and bordered by NG0207927 at the map position of 18.6 cM on left and by NG0207529 at the map position of 20.0 cM on right.

Example 3: Event Specific Endpoint TAQMAN® Assays

This example describes an event specific endpoint TAQMAN® thermal amplification method developed to identify event MON 88701 in a sample. Examples of conditions useful with the event MON 88701 Specific Endpoint TAQMAN® method are as follows: Step 1: 18 megohm water adjusted for final volume of 10 µl. Step 2: 5.0 µl of 2× Universal Master Mix (dNTPs, enzyme, buffer) to a 1× final concentration. Step 3: 0.5 µl Event Primer-1 (SQ21654) and Event Primer-2 (SQ23205). Mix (resuspended in 18 megohm water to a concentration of 20 uM for each primer) to 1.0 µM final concentration (for example in a microcentrifuge tube, the following should be added to achieve 500 µl at a final concentration of 20 uM: 100 µl of Primer SQ21654 at a concentration of 100 µM; 100 µl of Primer SQ23205 at a concentration of 100 µM; 300 µl of 18 megohm water). Step 4: 0.2 µl Event 6-FAM™ MGB Probe PB10280 (resuspended in 18 megohm water to a concentration of 10 µM to 0.2 µM final concentration. Step 5: 0.5 µl Internal Control Primer-1 and Internal Control Primer-2 Mix (resuspended in 18 megohm water to a concentration of 20 µM for each primer) to 1.0 µM final concentration. Step 6: 0.2 µl Internal Control VIC™ Probe to 0.2 µM final concentration (resuspended in 18 megohm water to a concentration of 10 µM) Step 7: 3.0 µl Extracted DNA (template) for each sample with one each of the following comprising 1. Leaf Samples to be analyzed; 2. Negative control (non-transgenic DNA); 3. Negative water control (no template); 4. Positive control MON 88701 DNA. Step 8: Thermocycler Conditions as follows: One Cycle at 50° C. for 2 minutes; One Cycle at 95° C. for 10 minutes; Ten Cycles of 95° C. for 15 seconds then 64° C. for 1 minute with −1° C./cycle; Thirty Cycles of 95° C. for 15 seconds then 54° C. 1 minute, optional additional 10 to 20 cycles (95° C. for 15 seconds then 64° C. for 1 minute (−1° C./cycle) may provide more distinct population separation during EndPoint TaqMan® analysis; final cycle of 10° C.

The DNA primers used in the endpoint assay are primers SQ21654 (SEQ ID NO: 11), SQ23205 (SEQ ID NO: 12), and 6-FAM™ labeled probe PB10280 (SEQ ID NO: 13). 6-FAM™ is a fluorescent dye product of Applied Biosystems (Foster City, Calif.) attached to the DNA probe. For TAQMAN® MGB™ probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence. SQ21654 (SEQ ID NO: 11) and SQ23205 (SEQ ID NO: 12) when used with these reaction methods with PB10280 (SEQ ID NO: 13) produce a DNA amplicon that is diagnostic for event MON 88701 DNA. The controls for this analysis should include a positive control from cotton containing event MON 88701 DNA, a negative control from non-transgenic cotton, and a negative control that contains no template DNA. Additionally, a control for the PCR reaction includes Internal Control Primers and an Internal Control Probe, specific to a single copy gene in the Gossypium genome. One of skill in the art will know how to design primers specific to a single copy gene in the Gossypium genome. These assays are optimized for use with either an Applied Biosystems GeneAmp® PCR System 9700 (run at maximum speed) or MJ Research DNA Engine PTC-225 thermal cycler. Other methods and apparatus known to those skilled in the art that produce amplicons that identify the event MON 88701 DNA is within the skill of the art.

R0 plants demonstrating the presence of the expression cassette were allowed to develop into fully mature plants and seed was harvested from these. Probes based on the sequence of the expression cassette were used to determine copy number of the transgenic expression cassette in the R1 plants using a combination of Southern analysis and end-point TAQMAN®.

A zygosity assay is useful for determining if a plant comprising an event is homozygous for the event DNA; that is comprising the exogenous DNA in the same location on each chromosome of a chromosomal pair; or heterozygous for an event DNA, that is comprising the exogenous DNA on only one chromosome of a chromosomal pair; or is null for the event DNA, that is wildtype. The endpoint TAQ-MAN® thermal amplification method was also used to develop zygosity assays for event MON 88701. This example describes an event-specific endpoint TAQMAN® thermal amplification method developed to determine the zygosity of event MON 88701 in a sample. For this assay, a three primer assay was employed wherein primer SQ21654 hybridizes and extends specifically from the 3' junction of the inserted exogenous DNA and genomic DNA, primer SQ23205 hybridizes and extends specifically from the DNA flanking the 3' side of the inserted exogenous DNA, and primer SQ23901 hybridizes and extends specifically from genomic DNA into which was integrated the inserted exogenous DNA. The three primers are diagnostic for the event. In this example, primer SQ21654 and primer SQ23205 and the 6-FAM™-labeled oligonucleotide probe PB10280 are diagnostic when there is a copy of the inserted exogenous DNA. In this example, SQ23205 and primer SQ23901 and the VIC™-labeled oligonucleotide probe PB10631 are diagnostic when there is no copy of the inserted exogenous DNA present in the genomic DNA, i.e. wild-type. When the three primers and two probes are mixed together in a PCR reaction with DNA extracted from a plant homozygous for event MON 88701, there is a fluorescent signal only from 6-FAM™-labeled oligonucleotide probe PB10280 which is indicative of and diagnostic for a plant homozygous for event MON 88701. When the three primers and two probes are mixed together in a PCR reaction with DNA extracted from a plant heterozygous for event MON 88701, there is a fluorescent signal from both the 6-FAM™-labeled oligonucleotide probe PB10280 and the VIC™-labeled oligonucleotide probe PB10631 which is indicative of and diagnostic for a plant heterozygous for event MON 88701. When the three primers and two probes are mixed together in a PCR reaction with DNA extracted from a plant which is null for event MON 88701 (i.e. wildtype), there is a fluorescent signal from only the VIC™-labeled oligo-nucleotide probe PB10631 which is indicative of and diagnostic for a plant null for event MON 88701, i.e. wild-type. Examples of conditions useful with this method are as follows. Step 1: 18 megohm water adjusted for final volume of 10 µl. Step 2: 5.0 µl of 2× Universal Master Mix (Applied Biosystems cat #4304437; dNTPs, enzyme, buffer) to a 1× final concentration. Step 3: 0.5 µl of Zygosity Primers SQ21654; SQ23205 and SQ23901 (resuspended in 18 megohm water to a concentration of 20 µM for each primer) to a final concentration of 1.0 µM. Step 4: 0.2 µl 6-FAM™ Probe PB10280 (resuspended in 18 megohm water to a concentration of 10 µM) to 0.2 µM final concentration. Step 5: 0.2 µl VIC™ Probe PB10631 (resuspended in 18 megohm water to a concentration of 10 µM) to 0.2 µM final concentration. Step 6: 3.0 µl Extracted DNA (template) for each sample with one each of the following comprising 1. Leaf Samples to be analyzed (4-5 ng/ul of genomic DNA diluted in water); 2. Negative control (non-transgenic cotton DNA; 5 ng/ul diluted in water); 3. Negative water control (no template; solution in which DNA was resuspended); 4. Positive control MON 88701 genomic DNA from known heterozygous sample (5 ng/ul diluted in water); 5. 4. Positive control MON 88701 genomic DNA from known homozygous sample (5 ng/ul diluted in water). Step 7: Gently mix. Step 8: Thermocycler Conditions when using Applied Biosystems GeneAmp® PCR System 9700 (run at maximum speed) or MJ Research DNA Engine PTC-225 thermal cycler are as follows: One Cycle at 50° C. for 2 minutes; one cycle at 95° C. for 10 minutes; Ten Cycles of (95° C. for 15 seconds then 64° C. for 1 minute (−1° C./cycle); Thirty Cycles of (95° C. for 15 seconds then 54° C. for 1 minute); Optional additional 10 to 20 cycles (95° C. for 15 seconds then 64° C. for 1 minute (−1° C./cycle) may provide more distinct population separation during EndPoint TaqMan® analysis; One cycle at 10° C. hold.

Example 4: Identification of Event MON 88701 in any Cotton Breeding Activity

This example describes how one may identify the MON 88701 event within progeny of any cotton breeding activity. DNA event primer pairs are used to produce an amplicon diagnostic for cotton event MON 88701. An amplicon diagnostic for MON 88701 comprises at least one of the sequences provided as SEQ ID NO: 1-10. Event primer pairs that will produce a diagnostic amplicon for MON 88701 include primer pairs based upon the flanking sequences and the inserted expression cassette. For example, to produce a diagnostic amplicon in which SEQ ID NO: 1 is found, one would design a forward primer based upon the genomic flanking sequence portion of SEQ ID NO: 7 and a reverse primer based upon the inserted expression cassette DNA sequence with the primers of sufficient length of contiguous nucleotides to specifically hybridize to the event DNA. To produce a diagnostic amplicon in which SEQ ID NO: 2 is found, one would design a forward primer based upon the inserted expression cassette DNA sequence and a reverse primer based upon the genomic flanking sequence portion of SEQ ID NO: 8 with the primers of sufficient length of contiguous nucleotides to specifically hybridize to the event DNA. For practical purposes, one should design primers which produce amplicons of a limited size range, for example, between 100 to 1000 bases. Smaller (shorter polynucleotide length) sized amplicons in general are more reliably produced in PCR reactions, allow for shorter cycle times, and can be easily separated and visualized on agarose gels or adapted for use in endpoint TAQMAN®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair that is useful in a DNA amplification method to produce an amplicon diagnostic for MON 88701 or plants comprising MONS 88701 or progeny thereof is an aspect of the invention. An example of the amplification conditions for this analysis is illustrated in Example 3.

An analysis for event MON 88701 containing plant tissue sample should include a positive tissue control from a plant comprising event MON 88701, a negative control from a cotton plant that does not contain event MON 88701 (for example, but not limited to Coker), and a negative control that contains no cotton genomic DNA. A primer pair that will amplify an endogenous cotton DNA molecule will serve as an internal control for the DNA amplification conditions. Additional primer sequences can be selected from SEQ ID NO: 10 by those skilled in the art of DNA amplification methods, and conditions selected for the production of an amplicon by the methods shown in Example 3 may differ, but result in an amplicon diagnostic for event MON 88701 DNA. DNA detection kits contain at least one DNA primer of sufficient length of contiguous nucleotides derived from SEQ ID NO: 10, that when used in a DNA amplification method produces a diagnostic amplicon for MON 88701 is an aspect of the invention.

A deposit of a representative sample of cotton seed comprising event MON 88701 has been made according to the Budapest Treaty with the American Type Culture Collection (ATCC) having an address at 10801 University Boulevard, Manassas, Va. USA, Zip Code 20110. The ATCC Patent Deposit Designation (accession number) for seeds comprising event MON 88701 is PTA-11754 and the date of deposit was Mar. 17, 2011. Access to the deposits will be available during the pendency of the application to the Commissioner of Patents and Trademarks and persons determined by the Commissioner to be entitled thereto upon request. The deposit will be maintained in the depository for a period of 30 years, or 5 years after the last request, or for the effective life of the patent, whichever is longer, and will be replaced as necessary during that period.

Having illustrated and described the principles of the invention, it should be apparent to persons skilled in the art that the invention can be modified in arrangement and detail without departing from such principles. We claim all modifications that are within the spirit and scope of the appended claims.

We claim:

1. A nonliving cotton plant material comprising a recombinant DNA molecule comprising the nucleotide sequence of SEQ ID NO:9 or SEQ ID NO:10.

2. A cotton commodity product comprising a recombinant DNA molecule comprising the nucleotide sequence of SEQ ID NO:9 or SEQ ID NO:10.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: artificial DNA sequence comprising cotton
      genomic sequence and transgene sequence

<400> SEQUENCE: 1
taggacatat tctcttaagg                                              20

<210> SEQ ID NO 2
<211> LENGTH: 20
<212> TYPE: DNA
<213> ORGANISM: Artificial Sequence
<220> FEATURE:
<223> OTHER INFORMATION: artificial DNA sequence comprising cotton
      genomic sequence and transgene sequence

<400> SEQUENCE: 2
acatgaagcc ttaattcaat                                              20

<210> SEQ ID NO 3
<211> LENGTH: 60
<212> TYPE: DNA
<213> ORGANISM: Artificial Sequence
<220> FEATURE:
<223> OTHER INFORMATION: artificial DNA sequence comprising cotton
      genomic sequence and transgene sequence

<400> SEQUENCE: 3
aaccttattt atataaaaat taggacatat tctcttaagg tagccaaagc ccgggcttaa    60

<210> SEQ ID NO 4
<211> LENGTH: 60
<212> TYPE: DNA
<213> ORGANISM: Artificial Sequence
<220> FEATURE:
<223> OTHER INFORMATION: artificial DNA sequence comprising cotton
      genomic sequence and transgene sequence

<400> SEQUENCE: 4
gatccatgta gatttcccgg acatgaagcc ttaattcaat attggctcta gaacataact    60

<210> SEQ ID NO 5
<211> LENGTH: 100
<212> TYPE: DNA
<213> ORGANISM: Artificial Sequence
<220> FEATURE:
<223> OTHER INFORMATION: artificial DNA sequence comprising cotton
``` genomic sequence and transgene sequence

<400> SEQUENCE: 5

| gttacaagaa catccttgat aaccttattt atataaaaat taggacatat tctcttaagg | 60 |
| tagccaaagc ccgggcttaa ttaaggcgcg ccggccaagt | 100 |

<210> SEQ ID NO 6
<211> LENGTH: 100
<212> TYPE: DNA
<213> ORGANISM: Artificial Sequence
<220> FEATURE:
<223> OTHER INFORMATION: artificial DNA sequence comprising cotton genomic sequence and transgene sequence

<400> SEQUENCE: 6

| tgaccatcat actcattgct gatccatgta gatttcccgg acatgaagcc ttaattcaat | 60 |
| attggctcta gaacataact tgtttaacac taaatataag | 100 |

<210> SEQ ID NO 7
<211> LENGTH: 1176
<212> TYPE: DNA
<213> ORGANISM: Artificial Sequence
<220> FEATURE:
<223> OTHER INFORMATION: artificial DNA sequence comprising cotton genomic sequence and transgene sequence

<400> SEQUENCE: 7

| cattatataa aaagaaaaat tttaaatata aaaaaatat attaaaacag tgaatcaaca | 60 |
| atcatgtctc ttaaaatgaa aaaattatc atttaaaatt tttaattaat aaaagtaaaa | 120 |
| tgaaattaaa acattttacc tgactttaac agtatagata attcaaaagt aaatatgatt | 180 |
| tcttctgatt tttcaaaaca aatttagaga ttataaatgc cattcgtcga tcattttgac | 240 |
| acgaaagatt taagaaaagc aaatgtaacc tttgacatga tgagcataat cacttcaaat | 300 |
| agtatttttt tttatttcca acgtcaatat attgaaatat tttttatag aataaactat | 360 |
| agcaattttt gccatgatgg ttcaacttat accactatcc ttaaccaata tattttgtt | 420 |
| tagacattag gagttaagtc tgatgtcgga tgttttgttc cttatttatt caggtgtttt | 480 |
| ataattttac ttatgaaaga ggttggtttt tctcaatgca tttctaatat catatataca | 540 |
| cattgattga gcaaaaaaaa aaaaaactat cctcaaccaa tgtagaagtg agttggttgc | 600 |
| atgatctttt atttgaattt tcaatattga aaaaactaaa accacatgtc ttaatccatc | 660 |
| gtaataatac tgctattatt tgaaaagttg atagcaaata ttacaataga aaatgtagat | 720 |
| ctataagaag aaagtatagc tatgtgaaat ctcatataac taatggtatg attaatgttg | 780 |
| attatattca aagtgttgat aatctcacat attctttgac aaaagcttta gttagagaaa | 840 |
| aaaatatgga tagtaataat gaggataaga ctaaagcctg aacaataata aaaatcaata | 900 |
| ataaggatac tttacataat gattagagat cccaaaaatt agattcaaaa ggaaaaatga | 960 |
| atacatattt aaaaaatctc tcttttcggt ataatgaatg tatgtataac aataatagaa | 1020 |
| gttgagtata actatactct taatgaggtc cataactagt ttgagtgaaa tgcagagtta | 1080 |
| caagaacatc cttgataacc ttatttatat aaaaattagg acatattctc ttaaggtagc | 1140 |
| caaagcccgg gcttaattaa ggcgcgccgg ccaagt | 1176 |

<210> SEQ ID NO 8
<211> LENGTH: 1188
<212> TYPE: DNA
<213> ORGANISM: Artificial Sequence

```
<220> FEATURE:
<223> OTHER INFORMATION: artificial DNA sequence comprising cotton
      genomic sequence and transgene sequence

<400> SEQUENCE: 8
tgaccatcat actcattgct gatccatgta gatttcccgg acatgaagcc ttaattcaat      60
attggctcta gaacataact tgtttaacac taaatataag tttatgccat tgacatatgt     120
ataatgcata actttctatc ttcacttgaa aagagagatt tactttcttc aaaatgtttg     180
tgtattaatt tagaagattt aaaccacgag acttgaagat tttaagatat cgatagattc     240
aagtacactt tcgcatatat tttatgttct taatgatttg acatgataaa actcggttta     300
tttagtttta tattataatt ttatgattgt aacacttaat tgataatgac atgatcaact     360
attaatttga caaaatcaaa agaaatagaa accgactttt cattttatgt ttagaatgaa     420
aaattcagtg tctaatttag atgagtcaaa tatttattca taattaggtc aggaatatac     480
ttaattactt gggtaaccaa aattggagtt tgattttcaa taattagatc aagttagtgt     540
tttaattact tataagaaaa ttttaatacc caaattacta atcaaatcta ttagaataaa     600
attagatgaa gatagaaaaa ttagctaata tatttaatga aaatttaatt ctaggtattt     660
actattgatt gattattctt tttgttagag ttatgtgacc tgaatcccgt ttgatctgat     720
ctgaaaagtt cgacgtacaa ttcatttgtc aaataaataa aataaagagg caaatagga      780
gatctgtata ggactatatt tcttcaatta acattgatt ctaaagggt tgtttaatcc       840
ttaaaatgcg tgtagtcgaa aacctcttgt attgtgattt tttaatatta gtgaatttct     900
cctcttctgt ccgtgatatt tcccgataag ggttttcaa ataaaacttg tgtattctta      960
tttttctttc ttattgtttt acgatccttc ctattgccat tatcgaagta tagtataaca    1020
cttttaaatc ttttaaaaat tatattatca attattttta taagttaaaa gaatataagt    1080
tacaaataat aattttttata ccatttatca cgaaatatat acttgcgggt acgatatttg   1140
tccacaaacc cttaacctcg tgttgagttg tgaacttcag ctatataa                 1188

<210> SEQ ID NO 9
<211> LENGTH: 4105
<212> TYPE: DNA
<213> ORGANISM: Artificial Sequence
<220> FEATURE:
<223> OTHER INFORMATION: artificial DNA sequence comprising transgene
      sequence

<400> SEQUENCE: 9
tctcttaagg tagccaaagc ccgggcttaa ttaaggcgcg ccggccaagt cggccgcggc      60
cgcgttaaca agcttctgca gaattcgtca acgagatctt gagccaatca agaggagtg     120
atgtagacct aaagcaataa tggagccatg acgtaagggc ttacgccat acgaaataat     180
taaaggctga tgtgacctgt cggtctctca gaacctttac ttttttatgtt tggcgtgtat    240
ttttaaattt ccacggcaat gacgatgtga cccaacgaga tcttgagcca atcaaagagg    300
agtgatgtag acctaaagca ataatggagc catgacgtaa gggcttacgc ccatacgaaa    360
taattaaagg ctgatgtgac ctgtcggtct ctcagaacct ttacttttta tatttggcgt    420
gtattttttaa atttccacgg caatgacgat gtgacctgtg catccgcttt gcctataaat    480
aagttttagt ttgtattgat cgacacggtc gagaagacac ggccattcta gttctcaaca    540
caacatatac aaaacaaacg aatctcaagc aatcaagcat tctacttcta ttgcagcaat    600
ttaaatcatt tcttttaaag caaaagcaat tttctgaaaa ttttcaccat ttacgaacga    660
```

```
tagccatggc gcaagttagc agaatctgca atggtgtgca gaacccatct cttatctcca    720
atctctcgaa atccagtcaa cgcaaatctc ccttatcggt ttctctgaag acgcagcagc    780
atccacgagc ttatccgatt cgtcgtcgt ggggattgaa gaagagtggg atgacgttaa    840
ttggctctga gcttcgtcct cttaaggtca tgtcttctgt ttccacggcg tgcatgctca    900
ctttcgttag aaacgcttgg tacgttgctg cacttcctga ggagttgagc gagaagcctc    960
taggaagaac tatcctcgat actccactag ctctctatcg tcaacctgac ggagttgtcg   1020
ctgccctgct tgatatttgt ccgcatcgct tcgctccgtt gagtgacggt attctagtca   1080
acggacatct ccagtgtcca tatcacggtc tggaatttga cggaggtggc cagtgtgtcc   1140
acaacccgca cggcaacgga gcccgccctg cttctctgaa cgtgcgatca ttccctgtcg   1200
tggaaagaga cgcattgatc tggatctggc ctggagatcc agcactcgca gatcccggtg   1260
ctatccctga ctttgggtgt cgtgttgatc cagcttaccg tactgtcgga ggttacggtc   1320
acgtggactg caactacaag ctccttgtgg ataacctcat ggatcttgga cacgctcagt   1380
acgtgcaccg cgctaacgcc caaacagacg ccttcgatag acttgagcgt gaggtgatcg   1440
ttggcgacgg cgagatccag gcgctcatga agatccctgg tggcacaccc tcagttctca   1500
tggctaagtt cttgcgtggt gctaacacac cagttgacgc ctggaacgac atccggtgga   1560
ataaggtgtc ggctatgctg aacttcatcg cggtcgcgcc ggaagggacg ccgaaggagc   1620
agtcaatcca ctcccgagga acccatatcc ttactcctga gaccgaggca agctgccatt   1680
acttcttcgg tagttcccgc aacttcggta tagacgatcc agagatggac ggtgttctca   1740
ggagctggca agctcaagcc ctggtgaagg aggacaaagt ggtcgttgaa gctatcgaaa   1800
ggcggagggc ttacgtcgaa gcgaacggga tcagacccgc catgttgtcc tgcgacgagg   1860
cagccgtcag ggtatccagg gagattgaga agctcgaaca actagaagcg gcgtgaggat   1920
ccactagtaa cggccgccag tgtgctggaa ttcgcccttg aattcaggcc tgatcacctg   1980
tcgtacagta tttctacatt tgatgtgtga tttgtgaaga acatcaaaca aaacaagcac   2040
tggctttaat atgatgataa gtattatggt aattaattaa ttggcaaaaa caacaatgaa   2100
gctaaaattt tatttattga gccttgcggt taatttcttg tgatgatctt ttttttttatt   2160
ttctaattat atatagtttc ctttgctttg aaatgctaaa ggtttgagag agttatgctc   2220
tttttttctt cctctttctt ttttaacttt atcatacaaa ttttgaataa aaatgtgagt   2280
acattgagct ctctgcaggt ccgattgaga cttttcaaca aagggtaata tccggaaacc   2340
tcctcggatt ccattgccca gctatctgtc actttattgt gaagatagtg gaaaaggaag   2400
gtggctccta caaatgccat cattgcgata aaggaaaggc catcgttgaa gatgcctctg   2460
ccgacagtgg tcccaaagat ggacccccac ccacgaggag catcgtggaa aaagaagacg   2520
ttccaaccac gtcttcaaag caagtggatt gatgtgatgg tccgattgag acttttcaac   2580
aaagggtaat atccggaaac ctcctcggat tccattgccc agctatctgt cactttattg   2640
tgaagatagt ggaaaaggaa ggtggctcct acaaatgcca tcattgcgat aaaggaaagg   2700
ccatcgttga agatgcctct gccgacagtg gtcccaaaga tggacccca cccacgagga   2760
gcatcgtgga aaagaagac gttccaacca cgtcttcaaa gcaagtggat tgatgtgata   2820
tctccactga cgtaagggat gacgcacaat cccactatcc ttcgcaagac ccttcctcta   2880
tataaggaag ttcatttcat ttggagaggc ctcagaaaaa tttgctacat tgtttcacaa   2940
acttcaaata ttattcattt atttgtcagc tttcaaactc tttgtttctt gtttgttgat   3000
tgagaatagg atccatgagc ccagaacgac gcccggccga catccgccgt gccaccgagg   3060
```

```
cggacatgcc ggcggtctgc accatcgtca accactacat cgagacaagc acggtcaact    3120
tccgtaccga gccgcaggaa ccgcaggagt ggacggacga cctcgtccgt ctgcgggagc    3180
gctatccctg gctcgtcgcc gaggtggacg gcgaggtcgc cggcatcgcc tacgcgggcc    3240
cctggaaggc acgcaacgcc tacgactgga cggccgagtc gaccgtgtac gtctcccccc    3300
gccaccagcg gacgggactg ggctccacgc tctacaccca cctgctgaag tccctggagg    3360
cacagggctt caagagcgtg gtcgctgtca tcgggctgcc caacgacccg agcgtgcgca    3420
tgcacgaggc gctcggatat gccccccgcg gcatgctgcg ggcggccggc ttcaagcacg    3480
ggaactggca tgacgtgggt ttctggcagc tggacttcag cctgccggta ccgccccgtc    3540
cggtcctgcc cgtcaccgag atctgagaat tgatcgttca acatttggc aataaagttt    3600 cttaagattg aatcctgttg ccggtcttgc gatgattatc atataatttc tgttgaatta    3660
cgttaagcat gtaataatta acatgtaatg catgacgtta tttatgagat gggttttat    3720 gattagagtc ccgcaattat acatttaata cgcgatagaa acaaaatat agcgcgcaaa    3780 ctaggataaa ttatcgcgcg cggtgtcatc tatgttacta gatcctcgag tggaggcctc    3840
atcctcatct aagcccccat ttggacgtga atgtagacac gtcgaaataa agatttccga    3900
attagaataa tttgtttatt gctttcgcct ataaatacga cggatcgtaa tttgtcgttt    3960
tatcaaaatg tactttcatt ttataataac gctgcggaca tctacatttt tgaattgaaa    4020
aaaaattggt aattactctt tcttttctc catattgacc atcatactca ttgctgatcc    4080
atgtagattt cccggacatg aagcc                                         4105

<210> SEQ ID NO 10
<211> LENGTH: 6369
<212> TYPE: DNA
<213> ORGANISM: Artificial Sequence
<220> FEATURE:
<223> OTHER INFORMATION: artificial DNA sequence comprising cotton
      genomic sequence and transgene sequence

<400> SEQUENCE: 10
cattatataa aagaaaaat tttaaatata aaaaaaatat attaaaacag tgaatcaaca      60
atcatgtctc ttaaaatgaa aaaaattatc atttaaaatt tttaattaat aaaagtaaaa    120
tgaaattaaa acattttacc tgactttaac agtatagata attcaaaagt aaatatgatt    180
tcttctgatt tttcaaaaca aatttagaga ttataaatgc cattcgtcga tcattttgac    240
acgaaagatt taagaaaagc aaatgtaacc tttgacatga tgagcataat cacttccaaat   300 agtatttttt tttatttcca acgtcaatat attgaaatat tttttatag aataaactat    360 agcaatttt gccatgatgg ttcaacttat accactatcc ttaaccaata tatttttgtt    420
tagacattag gagttaagtc tgatgtcgga tgttttgttc cttatttatt caggtgtttt    480
ataattttac ttatgaaaga ggttggtttt tctcaatgca tttctaatat catatataca    540
cattgattga gcaaaaaaaa aaaaactat cctcaaccaa tgtagaagtg agttggttgc    600
atgatctttt atttgaattt tcaatattga aaaaactaaa accacatgtc ttaatccatc    660
gtaataatac tgctattatt tgaaaagttg atagcaaata ttacaataga aaatgtagat    720
ctataagaag aaagtatagc tatgtgaaat ctcatataac taatggtatg attaatgttg    780
attatattca aagtgttgat aatctcacat attctttgac aaaagcttta gttagagaaa    840
aaaatatgga tagtaataat gaggataaga ctaaagcctg aacaataata aaaatcaata    900
ataaggatac tttacataat gattagagat cccaaaaatt agattcaaaa ggaaaaatga    960
```

```
atacatattt aaaaaatctc tcttttcggt ataatgaatg tatgtataac aataatagaa      1020
gttgagtata actatactct taatgaggtc cataactagt ttgagtgaaa tgcagagtta      1080
caagaacatc cttgataacc ttatttatat aaaaattagg acatattctc ttaaggtagc      1140
caaagcccgg gcttaattaa ggcgcgccgg ccaagtcggc cgcggccgcg ttaacaagct      1200
tctgcagaat tcgtcaacga gatcttgagc caatcaaaga ggagtgatgt agacctaaag      1260
caataatgga gccatgacgt aagggcttac gcccatacga aataattaaa ggctgatgtg      1320
acctgtcggt ctctcagaac ctttactttt tatgtttggc gtgtattttt aaatttccac      1380
ggcaatgacg atgtgaccca acgagatctt gagccaatca agaggagtg atgtagacct       1440 aaagcaataa tggagccatg acgtaagggc ttacgcccat acgaaataat taaaggctga      1500
tgtgacctgt cggtctctca gaacctttac tttttatatt tggcgtgtat ttttaaattt      1560
ccacggcaat gacgatgtga cctgtgcatc cgctttgcct ataaataagt tttagtttgt      1620
attgatcgac acggtcgaga agacacggcc attctagttc tcaacacaac atatacaaaa      1680
caaacgaatc tcaagcaatc aagcattcta cttctattgc agcaatttaa atcatttctt      1740
ttaaagcaaa agcaattttc tgaaaatttt caccatttac gaacgatagc catggcgcaa      1800
gttagcagaa tctgcaatgg tgtgcagaac ccatctctta tctccaatct ctcgaaatcc      1860
agtcaacgca aatctcccct tatcggtttct ctgaagacgc agcagcatcc acgagcttat     1920
ccgatttcgt cgtcgtgggg attgaagaag agtgggatga cgttaattgg ctctgagctt      1980
cgtcctctta aggtcatgtc ttctgttccc acggcgtgca tgctcacttt cgttagaaac      2040
gcttggtacg ttgctgcact tcctgaggag ttgagcgaga agcctctagg aagaactatc      2100
ctcgatactc cactagctct ctatcgtcaa cctgacggag ttgtcgctgc cctgcttgat      2160
atttgtccgc atcgcttcgc tccgttgagt gacggtattc tagtcaacgg acatctccag      2220
tgtccatatc acggtctgga atttgacgga ggtggccagt gtgtccacaa cccgcacggc      2280
aacggagccc gccctgcttc tctgaacgtg cgatcattcc ctgtcgtgga aagagacgca      2340
ttgatctgga tctggcctgg agatccagca ctcgcagatc ccggtgctat ccctgacttt      2400
gggtgtcgtg ttgatccagc ttaccgtact gtcggaggtt acggtcacgt ggactgcaac      2460
tacaagctcc ttgtggataa cctcatggat cttggacacg ctcagtacgt gcaccgcgct      2520
aacgcccaaa cagacgcctt cgatagactt gagcgtgagg tgatcgttgg cgacggcgag      2580
atccaggcgc tcatgaagat ccctggtggc acaccctcag ttctcatggc taagttcttg      2640
cgtggtgcta acacaccagt tgacgcctgg aacgacatcc ggtggaataa ggtgtcggct      2700
atgctgaact tcatcgcggt cgcgccggaa gggacgccga aggagcagtc aatccactcc      2760
cgaggaaccc atatccttac tcctgagacc gaggcaagct gccattactt cttcggtagt      2820
tcccgcaact tcggtataga cgatccagag atggacggtg ttctcaggag ctggcaagct      2880
caagccctgg tgaaggagga caaagtggtc gttgaagcta tcgaaaggcg gagggcttac      2940
gtcgaagcga acgggatcag acccgccatg ttgtcctgcg acgaggcagc cgtcagggta      3000
tccagggaga ttgagaagct cgaacaacta gaagcggcgt gaggatccac tagtaacggc      3060
cgccagtgtg ctggaattcg ccccttgaatt caggcctgat cacctgtcgt acagtatttc     3120
tacatttgat gtgtgatttg tgaagaacat caaacaaaac aagcactggc tttaatatga      3180
tgataagtat tatggtaatt aattaattgg caaaaacaac aatgaagcta aaattttatt      3240
tattgagcct tgcggttaat ttcttgtgat gatctttttt tttatttttct aattatatat     3300
```

```
agtttccttt gctttgaaat gctaaaggtt tgagagagtt atgctctttt tttcttcctc   3360
tttctttttt aactttatca tacaaatttt gaataaaaat gtgagtacat tgagctctct   3420
gcaggtccga ttgagacttt tcaacaaagg gtaatatccg gaaacctcct cggattccat   3480
tgcccagcta tctgtcactt tattgtgaag atagtggaaa aggaaggtgg ctcctacaaa   3540
tgccatcatt gcgataaagg aaaggccatc gttgaagatg cctctgccga cagtggtccc   3600
aaagatggac ccccacccac gaggagcatc gtggaaaaag aagacgttcc aaccacgtct   3660
tcaaagcaag tggattgatg tgatggtccg attgagactt ttcaacaaag ggtaatatcc   3720
ggaaacctcc tcggattcca ttgcccagct atctgtcact ttattgtgaa gatagtggaa   3780
aaggaaggtg gctcctacaa atgccatcat tgcgataaag gaaaggccat cgttgaagat   3840
gcctctgccg acagtggtcc caaagatgga ccccacccca cgaggagcat cgtggaaaaa   3900
gaagacgttc caaccacgtc ttcaaagcaa gtggattgat gtgatatctc cactgacgta   3960
agggatgacg cacaatccca ctatccttcg caagaccctt cctctatata aggaagttca   4020
tttcatttgg agaggcctca gaaaaatttg ctacattgtt tcacaaactt caaatattat   4080
tcatttattt gtcagctttc aaactctttg tttcttgttt gttgattgag aataggatcc   4140
atgagcccag aacgacgccc ggccgacatc cgccgtgcca ccgaggcgga catgccggcg   4200
gtctgcacca tcgtcaacca ctacatcgag acaagcacgg tcaacttccg taccgagccg   4260
caggaaccgc aggagtggac ggacgacctc gtccgtctgc gggagcgcta tccctggctc   4320
gtcgccgagg tggacggcga ggtcgccggc atcgcctacg cgggcccctg gaaggcacgc   4380
aacgcctacg actggacggc cgagtcgacc gtgtacgtct ccccccgcca ccagcggacg   4440
ggactgggct ccacgctcta cacccacctg ctgaagtccc tggaggcaca gggcttcaag   4500
agcgtggtcg ctgtcatcgg gctgcccaac gacccgagcg tgcgcatgca cgaggcgctc   4560
ggatatgccc cccgcggcat gctgcgggcg ccggcttca agcacgggaa ctggcatgac   4620
gtgggtttct ggcagctgga cttcagcctg ccggtaccgc cccgtccggt cctgcccgtc   4680
accgagatct gagaattgat cgttcaaaca tttggcaata aagtttctta agattgaatc   4740
ctgttgccgg tcttgcgatg attatcatat aatttctgtt gaattacgtt aagcatgtaa   4800
taattaacat gtaatgcatg acgttattta tgagatgggt ttttatgatt agagtcccgc   4860
aattatacat ttaatacgcg atagaaaaca aaatatagcg cgcaaactag gataaattat   4920
cgcgcgcggt gtcatctatg ttactagatc ctcgagtgga ggcctcatcc tcatctaagc   4980
ccccatttgg acgtgaatgt agacacgtcg aaataaagat ttccgaatta gaataatttg   5040
tttattgctt tcgcctataa atacgacgga tcgtaatttg tcgttttatc aaaatgtact   5100 ttcatttat aataacgctg cggacatcta cattttgaa ttgaaaaaaa attggtaatt   5160
actctttctt tttctccata ttgaccatca tactcattgc tgatccatgt agatttcccg   5220
gacatgaagc cttaattcaa tattggctct agaacataac ttgtttaaca ctaaatataa   5280
gtttatgcca ttgacatatg tataatgcat aactttctat cttcacttga aaagagagat   5340
ttactttctt caaatgtttt gtgtattaat ttagaagatt taaaccacga gacttgaaga   5400
ttttaagata tcgatagatt caagtacact ttcgcatata ttttatgttc ttaatgattt   5460
gacatgataa aactcggttt atttagtttt atattataat tttatgattg taacacttaa   5520
ttgataatga catgatcaac tattaatttg acaaaatcaa aagaaataga aaccgacttt   5580
tcattttatg tttagaatga aaaattcagt gtctaattta gatgagtcaa atatttattc   5640
ataattaggt caggaatata cttaattact tgggtaacca aaattggagt ttgattttca   5700
```
ataattagat caagttagtg ttttaattac ttataagaaa attttaatac ccaaattact    5760
aatcaaatct attagaataa aattagatga agatagaaaa attagctaat atatttaatg    5820
aaaatttaat tctaggtatt tactattgat tgattattct ttttgttaga gttatgtgac    5880
ctgaatcccg tttgatctga tctgaaaagt tcgacgtaca attcatttgt caaataaata    5940
aaataaagag gcaaaatagg agatctgtat aggactatat ttcttcaatt aaacattgat    6000
tctaaaaggg ttgtttaatc cttaaaatgc gtgtagtcga aaacctcttg tattgtgatt    6060
ttttaatatt agtgaatttc tcctcttctg tccgtgatat ttcccgataa gggttttttca   6120 aataaaactt gtgtattctt attttctttt cttattgttt tacgatccctt cctattgcca    6180 ttatcgaagt atagtataac acttttaaat cttttaaaaa ttatattatc aattattttt     6240
ataagttaaa agaatataag ttacaaataa taatttttat accatttatc acgaaatata   6300
tacttgcggg tacgatattt gtccacaaac ccttaacctc gtgttgagtt gtgaacttca    6360
gctatataa                                                            6369

<210> SEQ ID NO 11
<211> LENGTH: 24
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 11
gaccatcata ctcattgctg atcc                                           24

<210> SEQ ID NO 12
<211> LENGTH: 31
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 12
gtgttaaaca agttatgttc tagagccaat a                                   31

<210> SEQ ID NO 13
<211> LENGTH: 19
<212> TYPE: DNA
<213> ORGANISM: Artificial Sequence
<220> FEATURE:
<223> OTHER INFORMATION: Chemically Synthesized Oligonucleotide PCR
      Probe

<400> SEQUENCE: 13
tagatttccc ggacatgaa                                                 19

<210> SEQ ID NO 14
<211> LENGTH: 29
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 14
gaaatctatg tgtttgacac aatacacag                                      29

<210> SEQ ID NO 15

```
<211> LENGTH: 16
<212> TYPE: DNA
<213> ORGANISM: Artificial Sequence
<220> FEATURE:
<223> OTHER INFORMATION: Chemically Synthesized Oligonucleotide PCR
      Probe

<400> SEQUENCE: 15
ttccccaaag aagcct                                                      16
```